US008114966B2

(12) United States Patent
Nilsson et al.

(10) Patent No.: US 8,114,966 B2
(45) Date of Patent: Feb. 14, 2012

(54) PEPTIDE-BASED PASSIVE IMMUNIZATION THERAPY FOR TREATMENT OF ATHEROSCLEROSIS

(75) Inventors: Jan Nilsson, Genarp (SE); Roland Carlsson, Lund (SE); Jenny Bengtsson, Lund (SE); Leif Strandberg, Kavlinge (SE)

(73) Assignee: Forskarpatent I SYD AB, Lund (SE)

( * ) Notice: Subject to any disclaimer, the term of this patent is extended or adjusted under 35 U.S.C. 154(b) by 177 days.

(21) Appl. No.: 12/258,745

(22) Filed: Oct. 27, 2008

(65) Prior Publication Data
US 2009/0155258 A1 Jun. 18, 2009

Related U.S. Application Data

(62) Division of application No. 10/679,032, filed on Oct. 3, 2003, now Pat. No. 7,468,183.

(60) Provisional application No. 60/421,067, filed on Oct. 25, 2002.

(30) Foreign Application Priority Data

Oct. 4, 2002 (SE) ...................................... 0202959
Aug. 27, 2003 (SE) ...................................... 0302312

(51) Int. Cl.
C07K 16/00 (2006.01)
C12P 21/08 (2006.01)
A61K 39/395 (2006.01)
A61K 39/40 (2006.01)
A61K 39/00 (2006.01)
C07K 1/00 (2006.01)

(52) U.S. Cl. ............... 530/387.1; 530/387.3; 530/387.9; 530/388.1; 530/388.15; 530/388.25; 424/130.1; 424/132.1; 424/133.1; 424/139.1; 424/141.1; 424/142.1; 424/156.1; 424/158.1

(58) Field of Classification Search .................. None
See application file for complete search history.

(56) References Cited

U.S. PATENT DOCUMENTS

| 4,970,144 | A  | 11/1990 | Fareed et al.  |
| 5,494,791 | A  |  2/1996 | Cohen          |
| 5,861,276 | A  |  1/1999 | Kwak et al.    |
| 5,972,890 | A  | 10/1999 | Lees et al.    |
| 6,225,070 | B1 |  5/2001 | Witztum et al. |

FOREIGN PATENT DOCUMENTS

| EP | 0433088    |  6/1991 |
| EP | 0433088 A1 |  6/1991 |
| EP | 0433088 B1 |  6/1997 |
| JP | 4159300    |  6/1992 |
| WO | 97/4331    | 11/1997 |
| WO | 98/13385   |  4/1998 |
| WO | 98/32845   |  7/1998 |
| WO | 98/42751   | 10/1998 |
| WO | 9842751 A1 | 10/1998 |
| WO | 98/56938   | 12/1998 |
| WO | 99/08109   |  2/1999 |
| WO | 9908109 A2 |  2/1999 |
| WO | 99/18986   |  4/1999 |
| WO | 00/02920   |  1/2000 |
| WO | 01/32070 A2|  5/2001 |
| WO | 0132070 A2 |  5/2001 |
| WO | 01/64008 A2|  9/2001 |
| WO | 0164008 A2 |  9/2001 |
| WO | 02/080954 A1| 10/2002 |
| WO | 0280954 A1 | 10/2002 |

OTHER PUBLICATIONS

Ameli, Sean et al. "Effect of Immunization with Homologous LDL and Oxidized LDL on Early Atherosclerosis in Hypercholesterolemic Rabbits" Arterioscler. Thromb. Vasc. Biol., 16:1074-9, 1996.
Borrebaeck, Carl A.K. and Roland Carlsson. "Human Therapuetic Antibodies" Curr. Opin. Pharmacol., 1:404-8, 2001.
Bruce, David et al. "Human Apo-lipoprotein B from Normal Plasma Contains Oxidised Peptides" Int. J. Biochem. Cell. Biol., 1409-20, 1999.
Caligiuri, Giuseppina et al. Protective Immunity Against Atherosclerosis Carried by B Cells of Hypercholesterolemic Mice: J. Clin. Invest. 109:745-753, 2002.
Dimayuga, Paul et al. "Inhibitory Effect on Arterial Injuriy-Induced Neointimal Formation by Adobtive B-Cell Transfer in Rag-1 Knockout Mice" Arterioscler. Thromb Vasc. Biol. 22:644-9, 2002.
Fredikson, Gunilla Nordin et al. "Inhibition of Atherosclerosis in ApoE-Null Mice by Immunization with ApoB-100 Peptide Sequences" Arterioscler. Thromb Vasc. Biol. 23(5):879-84, 2003.
Fredrikson, Gunilla Nordin et al. "Atheroprotective Immunization with MDA-modified Apo B-100 Peptide Sequences is Associated with Activation of Th2 Specific Antibody Expression" Autoimmunity, 38:171-179, 2005.
Freigang, Stefan et al. "Immunization of LDL Receptor-Deficient Mice With Homologous Malondialdehyde-Modified and Native LDL Reduces Progression of Atherosclerosis by Mechanisms Other than Induction of High Titers of Antibodies to Oxidative Neoepitopes" Arterioscler. Thromb. Vasc. Biol. 1973—82, 1998.
George Jacob et al. "Hyperimmunization of Apo-E-deficient Mice with Homologous malondialdehyde Low Density Lipoprotein Suppresses Early Atherogenesis" Atherosclerosis, 138:147-52, 1998.
Griffiths, Andrew D. et al. "Isolation of High Affinity Human Antibodies Directly from Large Synthetic Repertoires" EMBO J., 13:3245-3260.
Hammer, Astrid et al. "Generation, Characterization, and Histochemical Application of Monoclonal Antibodies Selectively Recognizing Oxidatively Modified ApoB-Containing Serum Lipoproteins" Arterioscler. Thromb Vasc. Biol. 704-13, 1995.

(Continued)

Primary Examiner — Chun Dahle
(74) Attorney, Agent, or Firm — Gesmer Updegrove LLP

(57) ABSTRACT

The present invention relates to passive immunization for treating or preventing atherosclerosis using an isolated human antibody directed towards at least one oxidized fragment of apolipoprotein B in the manufacture of a pharmaceutical composition for therapeutical or prophylactical treatment of atherosclerosis by means of passive immunization, as well as method for preparing such antibodies, and a method for treating a mammal, preferably a human using such an antibody to provide for passive immunization.

4 Claims, 19 Drawing Sheets

OTHER PUBLICATIONS

Hoogenboom, Hennie R. and Greg Winter. "By-Passing Immunisation Human Antibodies from Synthetic Repertoires of Germline VH Gene Segments Rearranged in Vitro" J. Mol. Biol. 227, 381-388, 1992.

Jovinge, Stefan et al. "DNA Fragmentation and Ultrastructural Changes of Degenerating Cells in Atheroclerotic Lesions and Smooth Muscle Cells Exposed to Oxidised LDL in Vitro" Arterioscler. Thromb Vasc. Biol. 17:2225-31, 1997.

Li, Yili et al. "Three-Dimensional Structures of Free and Antigen-Bound Fab from Monoclonal Antilysozyme Antibody HyHEL-63" Biochemistry 39:6296-6309, 2000.

McCafferty, John et al. "Phage Antibodies: Filamentous Phage Displaying Antibody Variable Domains" Nature 348:552-4, 1990.

Merck Manual of Diagnosis and Therapy, 1999 17th Edition, pp. 1656-1657.

Milstein, C. and G. Kohler. "Continuous Cultures of Fused Cells Secreting Antibody of Predefined Specificity" Nature 256:495-7, 1975.

Neuberger, M.S. et al. "A Hapten-specific Chimaeric IgE Antibody with Human Physiological Effector Function" Nature 314:268-70, 1985.

Palinski, Wulf et al. "Low density Lipoprotein Undergoes Oxidative Modification in Vivo" Proc. Natl. Acad. Sci. USA, 86:1372-6, 1989.

Palinski, Wulf et al. "Immunization of Low Density Lipoprotein (LDL) Receptor-Deficient Rabbits with Homologous Malondialdehyde-Modified LDL Reduces Atherogenesis" Proc. Natl. Acad. Sci. USA, 92:821-5, 1995.

Reff, Michael E. and Cheryl Heard. "A Review of Modifications to Recombinant Antibodies: Attempt to Increase Efficacy in Oncology Applications" Crit. Rev. Oncol/Hematol. 40:25-35, 2001.

Regnstrom, Jan et al. "Effect of Probucol Treatment on the Susceptibility of Low Density Lipoprotein Isolated from Hypercholesterolemic Patients to Become Oxidatively Modified in Vitro" Atherosclerosis 82: 43-51, 1990.

Schiopu, Alexandru, et al. "Recombinant Human Antibodies Against Aldehyde-Modified Apolipoprotein B-100 Peptide Sequences Inhibit Atherosclerosis" Circulation 110:2047-2052, 2004.

Schiopu, Alexandru, et al. "Sa.119. Plaque Regression Induced by Human Recombinant Antibodies Against Oxidized Low Density Lipoproteins in LDLR-/-Apobec-1 Double Knockout Mice" Clin. Immunol. 119:S147-8, 2006.

Schiopu, Alexandru, et al. "Plaque Regression Induced by Human Recombinant Antibodies Against Oxidized Low Density Lipoproteins in LDLR-/-Apobec-1 Double Knockout Mice" Poster:Clin. Immunol. 119:S147-8, 2006.

Shaw, Peter X., et al. "Human-Derived Anti-Oxidized LDL Autoantibody Blocks Uptake of Oxidized LDL by Macrophages and Localizes to Atherosclerotic Lesions in Vivo" Arterioscler. Thromb Vasc. Biol. 21:1333-1339, 2001.

Soderlind, Eskil et al. "Recombining Germline-Derived CDR Sequences for Creating Diverse Single-Framework Antibody Libraries" Nature BioTechnol. 18:852-6, 2000.

Soderlind, Eskil et al. "The Immune Diversity in a Test Tube-Non-Immunised Antibody Libraries and Functional Variability in Defined Protein Scaffolds" Comb. Chem & High Throughput Screen 4:409-16 2001.

Steinberg, Daniel et al. "Beyond Cholesterol: Modifications of Low-Density Lipoprotein That Increases Its Atherogenicity" New ENgland J. Med., 320:915-924, 1989.

Reff et al., "A review of modifications to recombinant antibodies: attempt to increase efficacy in oncology applications" Oncology Hematology, (2001) pp. 25-35.

The Merck Manual of Diagnosis and Therapy. 17th Edition, published by Merck Research Laboratories, 1999, pp. 1654-1659.

Tinahones et al. "Influence of age and sex on levels of anti-oxidized LDL antibodies and anti-LDL immune complexes in the general population" Journal of Lipid Research, vol. 46, 2005, pp. 452-457.

Li et al., "Three-Dimensional Structures of the Free and Antigen-Bound Fab from the Monoclonal Antilysozyme Antibody HyHEL-63" Biochemistry 2000, pp. 6296-6309.

Declaration of Dr. Bo Jansson, 3 pages signed Jul. 20, 2009.

Falk et al., "Coronary Plaque Disruption." Journal of the American Heart Association, 1995, pp. 657-671 (51 printed pages), vol. 92, American Heart Association, USA.

Lee et al., "The Unstable Atheroma, Arteriosclerosis, Thrombosis, and Vascular Biology." 1997, pp. 1859-1867 (35 printed pages), vol. 17, American Heart Association, USA.

Steinburg et al., "Lipoproteins, Lipoprotein Oxidation, and Atherogenesis." Molecular Basis of Cardiovascular Disease, 1999, pp. 458-475, WB Saunders Company, USA.

Superko et al., "Coronary Artery Disease Regression. Convincing Evidence for the Benefit of Aggressive Lipoprotein Management." Circulation 1994, pp. 1056-1069, vol. 90, American Heart Association, USA.

Schiopu et al., "Recombinant Antibodies to an Oxidized Low-Density Lipoprotein Epitope Induce Rapid Regression of Atherosclerosis in Apobec-1// Low-Density Lipoprotein Receptor/ Mice." Journal of the American College of Cardiology, Nov. 22, 2007, pp. 2313-2318 (8 pages printed), vol. 50, No. 24, USA.

Valentinova, N. V., Gu, Z., Yang, M., Yanushevskaya, E. V., Antonov, I. V., Guyton, J. R., Smith, C. V., Gotto, A. M. Jr. and Yang, C., "Immunoreactivity of Apolipoprotein B-100 in Oxidatively Modified Low Density Lipoprotein," Oct. 1994. pp. 651-658, Biol. Chem. vol. 375.

Hammer, A., Kager, G., Dohr, G., Rabl, H., Ghassempur, I. and Jurgens, G., "Generation, Characterization, and Histochemical Application of Monoclonal Antibodies Selectivity Recognizing Oxidatively Modified ApoB-Containing Serum Lipoproteins," 1995. 10 pgs, Arterioscler Throm Vasc Biol., vol. 15, pp. 704-713.

Bruce, D., Fu, S., Aemstrong, S. and Dean, R. T., "Human Apo-Lipoprotein B from Normal Plasma Contains Oxidised Peptides," Apr. 1999. pp. 1409-1420, JBC vol. 31.

NCBI Database acc. No. 1211338A, Aug. 16, 1996.
GENSEQ Database acc. No. A67477, May 5, 1999.
GENSEQ Database acc. No. AAW57204, Sep. 30, 2005.
GENSEQ Database acc. No. AAE14542, Sep. 29, 2009.
GENSEQ Database acc. No. AAW96865.1, Feb. 14, 2005.
GENSEQ Database acc. No. AAW96841, Feb. 14, 2005.
GENSEQ Database acc. No. AAW96832, Feb, 14, 2005.
GENSEQ Database acc. No. AAY09371, Apr. 20, 2005.
GENSEQ Database acc. No. AAY55851, Dec. 23, 2005.
GENSEQ Database acc. No. AAW96834, Feb. 14, 2005.
GENSEQ Database acc. No. AAW96836, Patented Feb. 14, 2005.

FIG. 1 cont'd
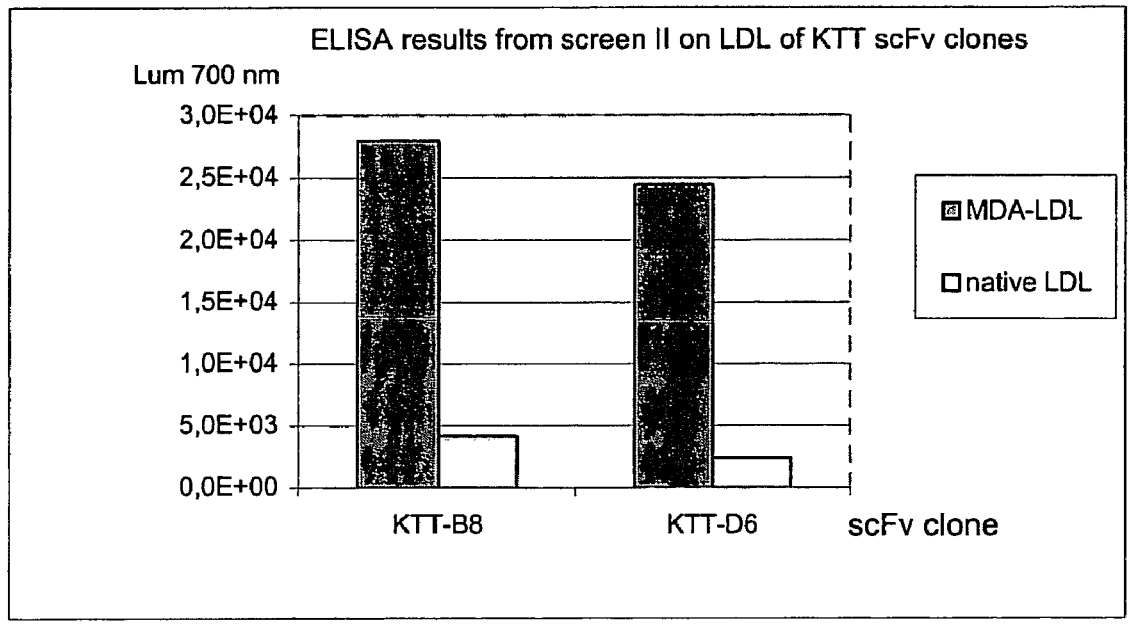
FIG. 1C
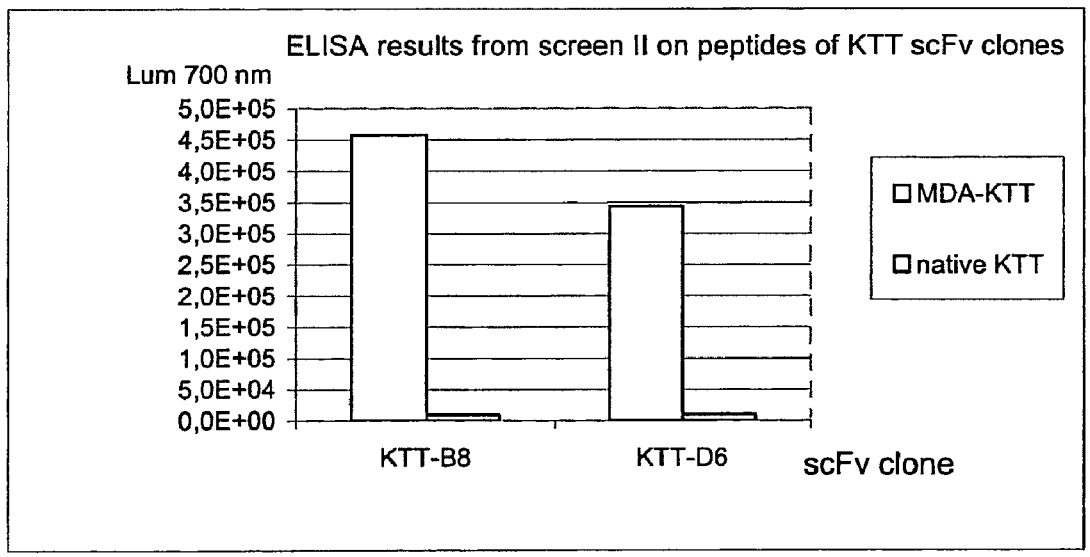
FIG. 1D

FIG. 2
Results from screening III titration of scFv on MDA modified LDL and non-modified native LDL
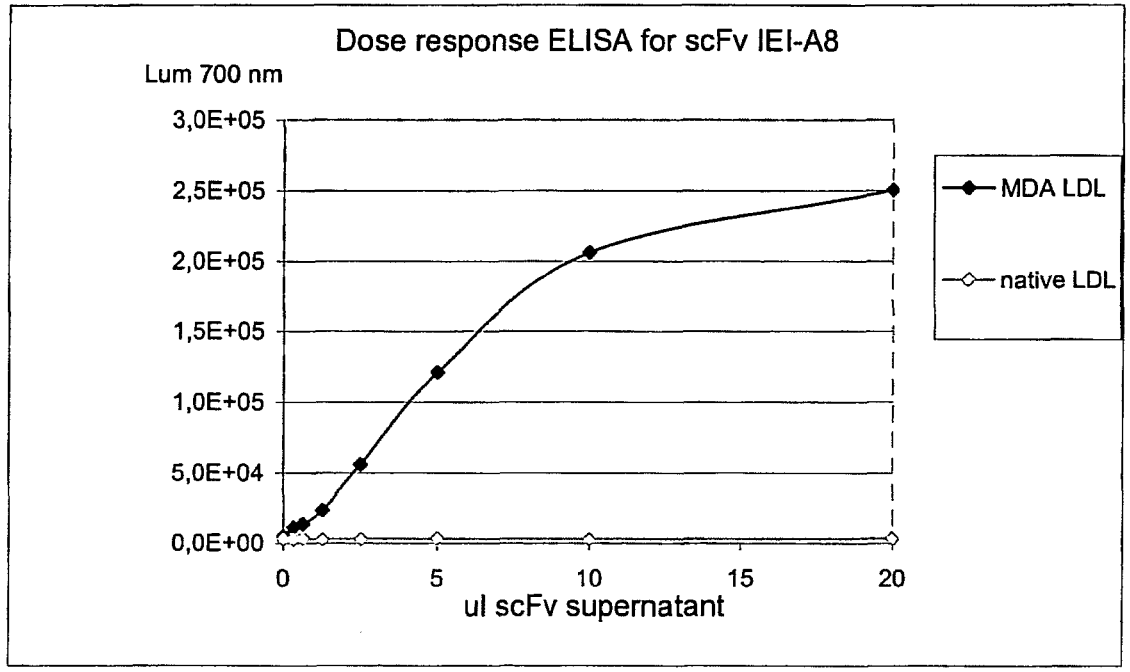
FIG. 2A
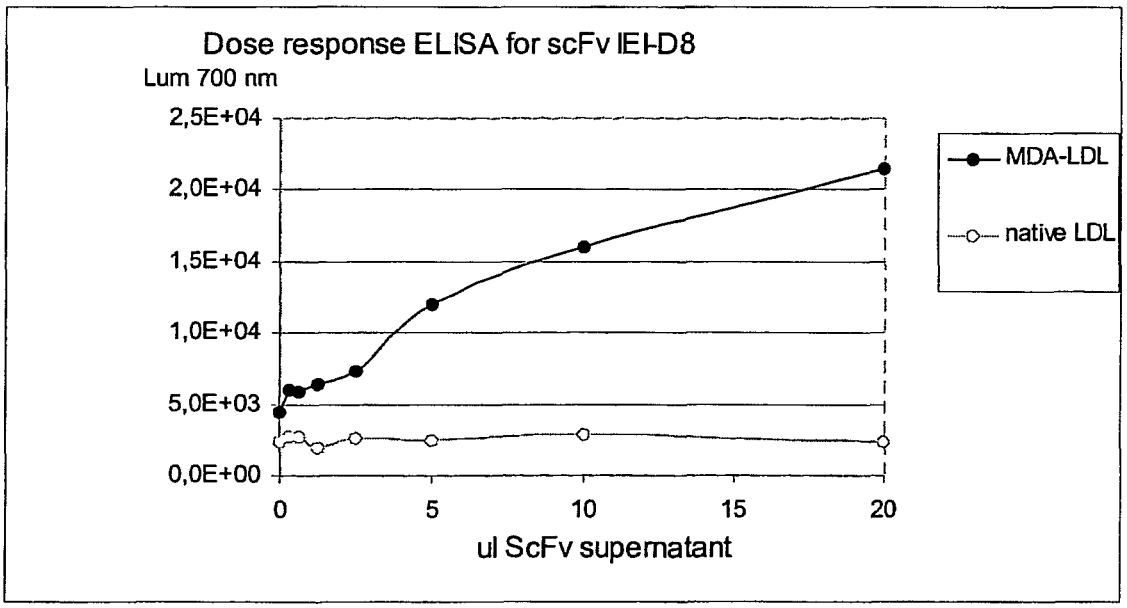
FIG. 2B FIG. 2 cont'd
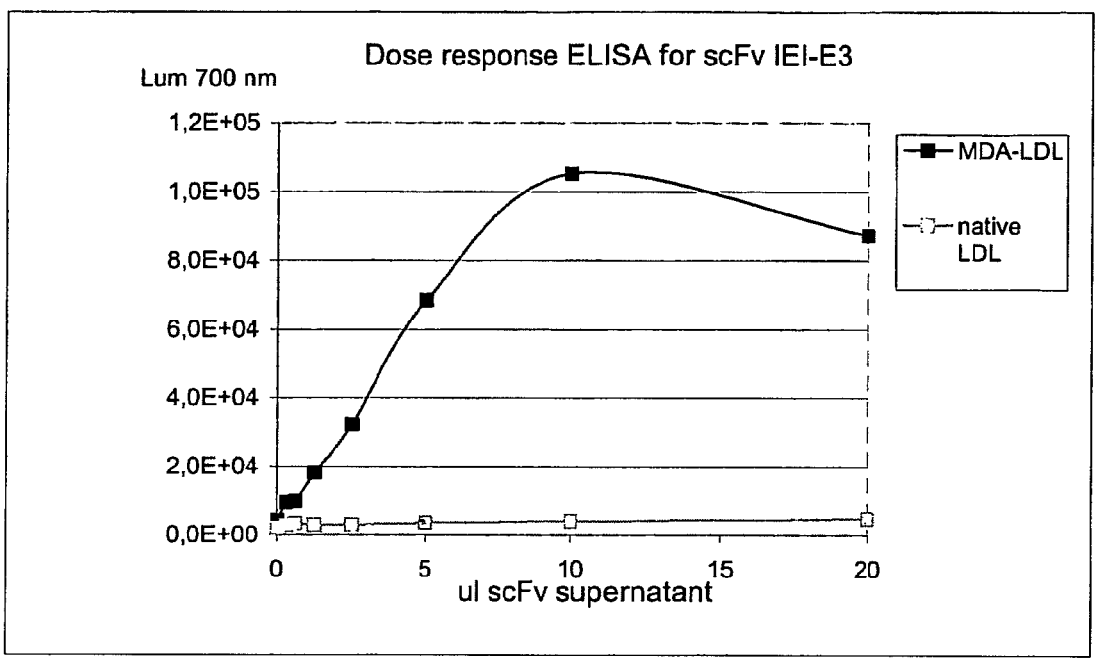
FIG. 2C
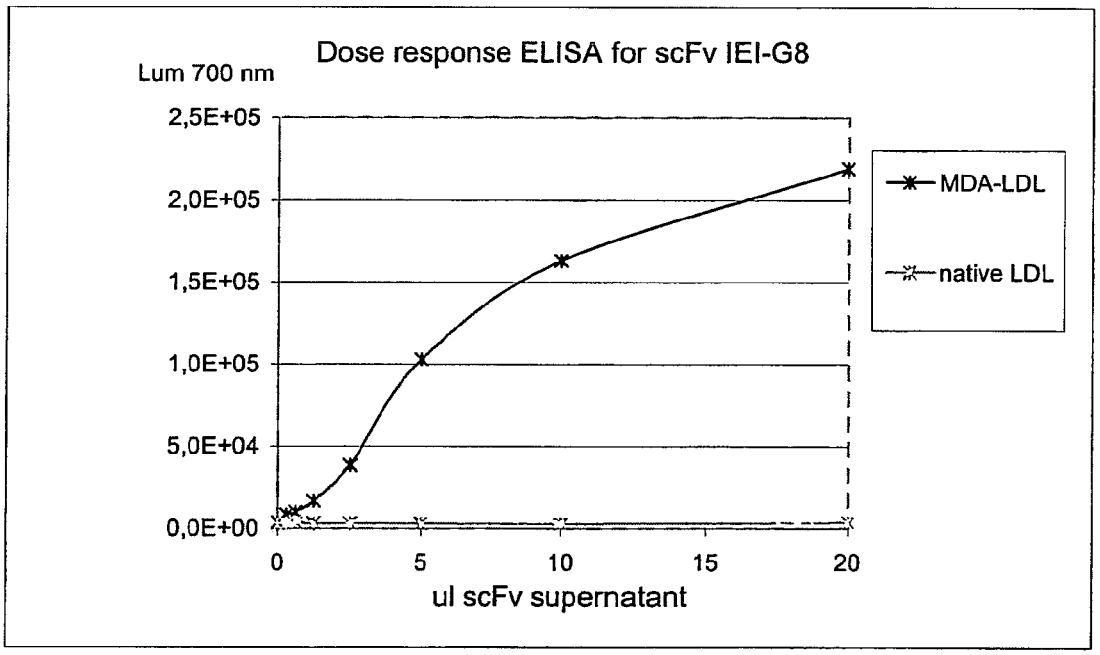
FIG. 2D FIG. 2 cont'd
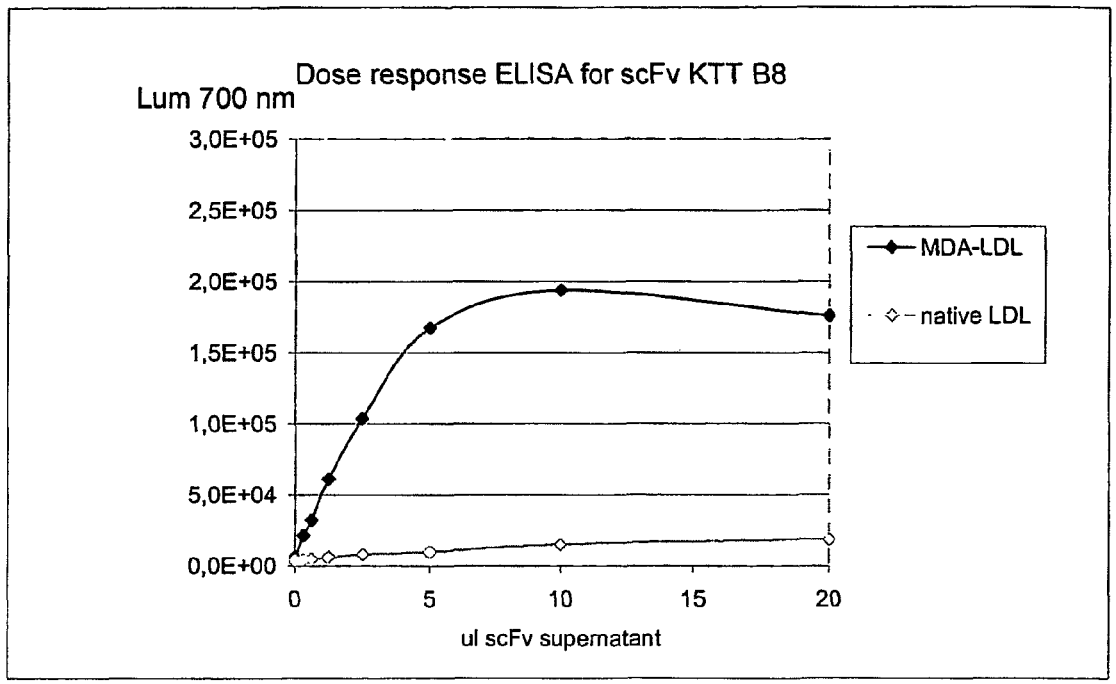
FIG. 2E
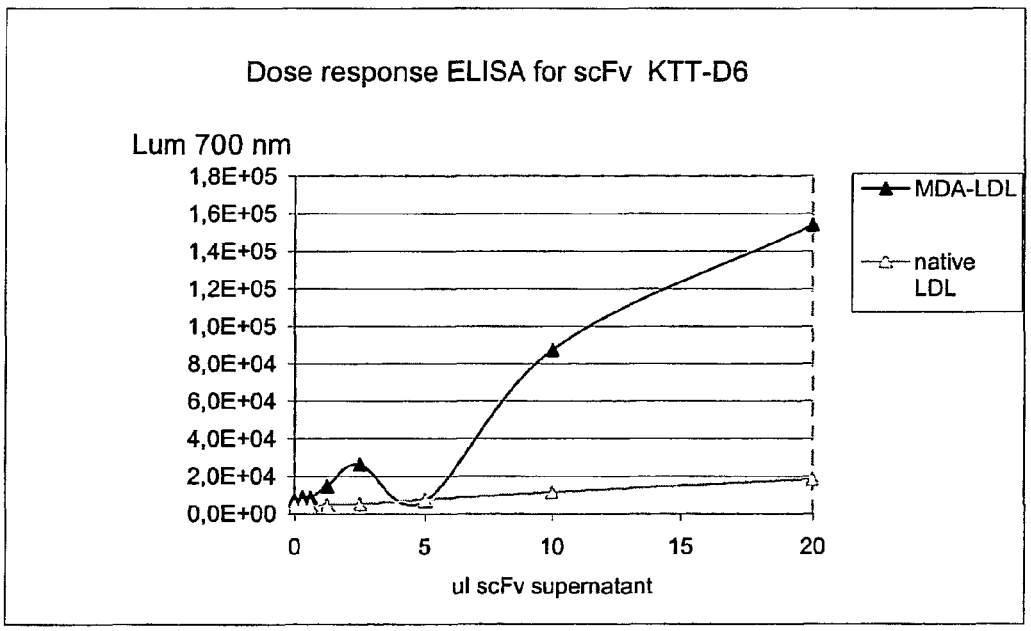
FIG. 2F

FIG. 3

DNA sequences of the variable regions in the six scFv that bind MDA modified ApoB-100 peptides.

IEIA8

Variable heavy region ($V_H$)
GAGGTGCAGCTGTTGGAGTCTGGGGGAGGCTTGGTACAGCCTGGGGGGTCCCTGAGACTCTC
CTGTGCAGCCTCTGGATTCACCTTCAATAACGCCTGGATGAGCTGGGTCCGCCAGGCTCCAGG
GAAGGGGCTGGAGTGGGTCTCATCCATTAGTAGTAGTAGTAGTTACATATACTACGCAGACTCA
GTGAAGGGCCGATTCACCATCTCCAGAGACAATTCCAAGAACACGCTGTATCTGCAAATGAACA
GCCTGAGAGCCGAGGACACTGCCGTGTATTACTGTGCGAGAGTCAGTAGGTACTACTACGGAC
CATCTTTCTACTTTGACTCCTGGGGCCAGGGTACACTGGTCACCGTGAGCAGC (SEQ ID NO: 1)

Variable light region ($V_L$)
CAGTCTGTGCTGACTCAGCCACCCTCAGCGTCTGGGACCCCCGGGCAGAGGGTCACCATCTCC
TGCTCTGGAAGCAGGTCCAACATTGGGAATAATTATGTATCCTGGTATCAGCAGCTCCCAGGAA
CGGCCCCCAAACTCCTCATCTATGGTAACAACAATCGGCCCTCAGGGGTCCCTGACCGATTCTC
TGGCTCCAAGTCTGGCACCTCAGCCTCCCTGGCCATCAGTGGGCTCCGGTCCGAGGATGAGGC
TGATTATTACTGTGCAGCATGGGATGACAGCCTGAATGGTCATTGGGTGTTCGGCGGAGGAAC
CAAGCTGACGGTCCTAGGT(SEQ ID NO: 2)

IEI-E3

Variable heavy region ($V_H$)
GAGGTGCAGCTGTTGGAGTCTGGGGGAGGCTTGGTACAGCCTGGGGGGTCCCTGAGACTCTC
CTGTGCGGCCTCTGGATTCACCTTCAGTGACTACTACATGAGCTGGGTCCGCCAGGCTCCCGG
GAAGGGGCTGGAGTGGGTATCGGGTGTTAGTTGGAATGGCAGTAGGACGCACTATGCAGACT
CTGTGAAGGGCCGATTCACCATCTCCAGAGACAATTCCAAGAACACGCTGTATCTGCAAATGAA
CAGCCTGAGAGCCGAGGACACTGCCGTGTATTACTGTGCGAGAGCGGCTAGGTACTCCTACTA
CTACTACGGTATGGACGTCTGGGGCCAAGGTACACTGGTCACCGTGAGCAGC (SEQ ID NO: 3)

Variable light region ($V_L$)
CAGTCTGTGCTGACTCAGCCACCCTCAGCGTCTGGGACCCCCGGGCAGAGGGTCACCATCTCC
TGTTCTGGAAGCAGCTCCAACATCGGAAATAATGCTGTAAACTGGTATCAGCAGCTCCCAGGAA
CGGCCCCCAAACTCCTCATCTATGGGAATGATCGGCGGCCCTCAGGGGTCCCTGACCGATTCT
CTGGCTCCAAGTCTGGCACCTCAGCCTCCCTGGCCATCAGTGGGCTCCGGTCCGAGGATGAGG
CTGATTATTACTGTCAGACCTGGGGCACTGGCCGGGGGTATTCGGCGGAGGAACCAAGCTGA
CGGTCCTAGGT(SEQ ID NO: 4)

IEI-G8

Variable heavy region (V$_H$)
GAGGTGCAGCTGTTGGAGTCTGGGGGAGGCTTGGTACAGCCTGGGGGGTCCCTGAGACTCTC
CTGTGCAGCCTCTGGATTCACCTTTAGTAGCTATTGGATGAGCTGGGTCCGCCAGGCTCCAGG
GAAGGGGCTGGAGTGGGTCTCAAGTATCAGTGGTAGTGGTCGTAGGACATACTACGCAGACTC
CGTGCAGGGCCGGTTCACCATCTCCAGAGACAATTCCAAGAACACGCTGTATCTGCAAATGAAC
AGCCTGAGAGCCGAGGACACTGCCGTGTATTACTGTGCGAGATTGGTCTCCTATGGTTCGGGG
AGTTTCGGTTTTGACTACTGGGGCCAAGGTACACTGGTCACCGTGAGCAGC (SEQ ID NO: 5)

Variable light region (V$_L$)
CAGTCTGTGCTGACTCAGCCACCCTCAGCGTCTGGGACCCCCGGGCAGAGGGTCACCATCTCT
TGTTCTGGAAGCAGCTCCAATATCGGAAGTAATTATGTATCCTGGTATCAGCAGCTCCCAGGAA
CGGCCCCCAAACTCCTCATCTATGGTAACTACAATCGGCCCTCAGGGGTCCCTGACCGATTCTC
TGGCTCCAAGTCTGGCACCTCAGCCTCCCTGGCCATCAGTGGGCTCCGGTCCGAGGATGAGGC
TGATTATTACTGTGCAGCATGGGATGACAGCCTGAGTGGTTGGGTGTTCGGCGGAGGAACCAA
GCTGACGGTCCTAGGT (SEQ ID NO: 6)

IEI-D8

Variable heavy region (V$_H$)
GAGGTGCAGCTGTTGGAGTCTGGGGGAGGCTTGGTACAGCCTGGGGGGTCCCTGAGACTCTC
CTGTGCAGCCTCTGGATTCACCTTCAGTAACGCCTGGATGAGCTGGGTCCGCCAGGTTCCAGG
GAAGGGGCTGGAGTGGGTCTCAACTCTTGGTGGTAGTGGTGGTGGTAGCACATACTACGCAGA
CTCCGTGAAGGGCCGGTTCACCATCTCCAGAGACAATTCCAAGAACACGCTGTATCTGCAAATG
AACAGCCTGAGAGCCGAGGACACTGCCGTGTATTACTGTGCGAAGTTAGGGGGGCGATCCCGA
TATGGGCGGTGGCCCCGCCAATTTGACTACTGGGGCCAAGGTACACTGGTCACCGTGAGCAGC
(SEQ ID NO: 7)

Variable light region (V$_L$)
CAGTCTGTGCTGACTCAGCCACCCTCAGCGTCTGGGACCCCCGGGCAGAGGGTCACCATCTCC
TGCTCTGGAAGCAGCTCCAACATTGGAAATAACTATGTATCCTGGTATCAGCAGCTCCCAGGAA
CGGCCCCCAAACTCCTCATCTATAGTAATAATCAGCGGCCCTCAGGGGTCCCTGACCGATTCTC
TGGCTCCAAGTCTGGCACCTCAGCCTCCCTGGCCATCAGTGGGCTCCGGTCCGAGGATGAGGC
TGATTATTACTGTGCAGCATGGGATGACAGCCTGAGTCATTGGCTGTTCGGCGGAGGAACCAA
GCTGACGGTCCTAGGT (SEQ ID NO: 8)

KTT-D6

Variable heavy region (V$_H$)
GAGGTGCAGCTGTTGGAGTCTGGGGGAGGCTTGGTACAGCCTGGGGGGTCCCTGAGACTCTC
CTGTGCAGCCTCTGGATTCACCTTCAGTGACTACTACATGAGCTGGATCCGCCAGGCTCCAGGG
AAGGGGCTGGAGTGGGTCTCAAGTATCAGTGGCCGTGGGGGTAGTTCCTACTACGCAGACTCC
GTGAGGGGCCGGTTCACCATCTCCAGAGACAATTCCAAGAACACGCTGTATCTGCAAATGAACA
GCCTGAGAGCCGAGGACACTGCCGTGTATTACTGTGCGAGACTTTCCTACAGCTATGGTTACGA
GGGGGCCTACTACTTTGACTACTGGGGCCAGGGTACACTGGTCACCGTGAGCAGC (SEQ ID NO: 9)

Variable light region (V<sub>L</sub>)
CAGTCTGTGCTGACTCAGCCACCCTCAGCGTCTGGGACCCCCGGGCAGAGGGTCACCATCTCC
TGCTCTGGAAGCAGCTCCAACATTGGGAATAATTATGTATCCTGGTATCAGCAGCTCCCAGGAA
CGGCCCCCAAACTCCTCATCTATAGGAATAATCAGCGGCCCTCAGGGGTCCCTGACCGATTCTC
TGGCTCCAAGTCTGGCACCTTAGCCTCCCTGGCCATCAGTGGGCTCCGGTCCGAGGATGAGGC
TGATTATTACTGTGCAACCTGGGATGACAGCCTGAATGGTTGGGTGTTCGGCGGAGGAACCAA
GCTGACGGTCCTAGGT (SEQ ID NO: 10)

KTT-B8

Variable heavy region (V<sub>H</sub>)
GAGGTGCAGCTGTTGGAGTCTGGGGGAGGCTTGGTACAGCCTGGGGGGTCCCTGAGACTCTC
CTGTGCAGCCTCTGGATTCACCTTTAGCAGCTATGCCATGAGCTGGGTCCGCCAGGCTCCAGG
GAAGGGGCTGGAGTGGGTCTCATCCATTAGTAGTAGTGGTCGTTTCATTTACTACGCAGACTCA
ATGAAGGGCCGCTTCACCATCTCCAGAGACAATTCCAAGAACACGCTGTATCTGCAAATGAACA
GCCTGAGAGCCGAGGACACTGCCGTGTATTACTGTACGAGGCTCCGGAGAGGGAGCTACTTCT
GGGCTTTTGATATCTGGGGCCAAGGTACACTGGTCACCGTGAGCAGC (SEQ ID NO: 11)

Variable light region (V<sub>L</sub>)
CAGTCTGTGCTGACTCAGCCACCCTCAGCGTCTGGGACCCCCGGGCAGAGGGTCACCATCTCC
TGTTCTGGAAGCAGCTCCAACATTGGCGGTGAGTCTGTATCCTGGTATCAGCAGCTCCCAGGAA
CGGCCCCCAAACTCCTCATCTATAGTAATAATCAGCGGCCCTCAGGGGTCCCTGACCGATTCTC
TGGCTCCAAGTCTGGCACCTCAGCCTCCCTGGCCATCAGTGGGCTCCGGTCCGAGGATGAGGC
TGATTATTACTGTGCAGCATGGGATGACAGCCTGAATGGTTGGGTGTTCGGCGGAGGAACCAA
GCTGACGGTCCTAGGT (SEQ ID NO: 12)

1-B12

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTTAGAACGTATTGGATGACCTGGGTCCGCCAGGCT
CCAGGGAAGGGGCTGGAGTGGGTCTCATCTATTAGCAGTAGCAGTAATTACATATTCTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGACTCAGA
CGGAGCAGCTGGTACGGGGGGTACTGGTTCGACCCCTGGGGCCAAGGTACACTGGTCACC
GTGAGCTCA (SEQ ID NO: 19)

Variable light (V<sub>L</sub>) region
CAGTCTGTGCTGACTCAGCCACCCTCAGCGTCTGGGACCCCCGGGCAGAGGGTCACCATC
TCCTGCTCTGGAAGCAGCTCCAACATTGGGAATAATTATGTATCCTGGTATCAGCAGCTC
CCAGGAACGGCCCCCAAACTCCTCATCTATAGGAATAATCAGCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGAATGGTCATTGG
GTGTTCGGCGGAGGAACCAAGCTGACGGTCCTAGGT (SEQ ID NO: 20)

Clone: 1-C07

Variable heavy (V$_H$) region
GAGGTGCAGCTGTTGGAGTCTGGGGGAGGCTTGGTACAGCCTGGGGGGTCCCTGAGACTCT
CCTGTGCAGCCTCTGGATTCACCTTCAGTAGCAACTACATGAGCTGGGTCCGCCAGGCTCC
AGGGAAGGGGCTGGAGTGGGTCTCATCCATTAGTAGTAGTAGTAGTTACATATACTACGCA
GACTCAGTGAAGGGCCGATTCACCATCTCCAGAGACAATTCCAAGAACACGCTGTATCTGC
AAATGAACAGCCTGAGAGCCGAGGACACTGCCGTGTATTACTGTGCGAGAGTAGGCCGGTA
TAACTGGAAGACGGGGCATGCTTTTGATATCTGGGGCCAGGGTACACTGGTCACCGTGAGC
TCA (SEQ ID NO: 21)

Variable light region (V$_L$)
CAGTCTGTGCTGACTCAGCCACCCTCAGCGTCTGGGACCCCCGGGCAGAGGGTCACCATCT
CCTGCTCTGGAAGGACCTACAACATTGGAAATAATTATGTATCGTGGTATCAGCAGCTCCC
AGGAACGGCCCCCAAACTCCTCATCTATGGTAACATCAATCGGCCCTCAGGGGTCCCTGAC
CGATTCTCTGGCTCCAAGTCTGGCACCTCAGCCTCCCTGGCCATCAGTGGGCTCCGGTCCG
AGGATGAGGCTGATTATTACTGTGCAGCATGGGATGTCAGGCTGAATGGTTGGGTGTTCGG
CGGAGGAACCAAGCTGACGGTCCTAGGT (SEQ ID NO: 22)

Clone: 1-C12

Variable heavy (V$_H$) region
GAGGTGCAGCTGTTGGAGTCTGGGGGAGGCTTGGTACAGCCTGGGGGGTCCCTGAGACTC
TCCTGTGCAGCCTCTGGATTCACCTTCCGTGACTACTACGTGAGCTGGATCCGCCAGGCT
CCAGGGAAGGGGCTGGAGTGGGTCTCAAGTATTAGTGGTAGTGGGGGTAGGACATACTAC
GCAGACTCCGTGGAGGGCCGGTTCACCATCTCCAGAGACAATTCCAAGAACACGCTGTAT
CTGCAAATGAACAGCCTGAGAGCCGAGGACACTGCCATGTATTACTGTGCCAGAGTATCC
GCCCTTCGGAGACCCATGACTACAGTAACTACTTACTGGTTCGACCCCTGGGGCCAAGGT
ACACTGGTCACCGTGAGCTCA (SEQ ID NO:23)

Variable light region (V$_L$)
CAGTCTGTGCTGACTCAGCCACCCTCAGCGTCTGGGACCCCCGGGCAGAGGGTCACCATC
TCCTGCTCTGGAAGGAGCTCCAACATTGGGAATAGTTATGTCTCCTGGTATCAGCAGCTC
CCAGGAACGGCCCCCAAACTCCTCATCTATAGGAATAATCAGCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGGATGGGATGACACCCTGCGTGCTTGGGTG
TTCGGCGGAGGAACCAAGCTGACGGTCCTAGGT (SEQ ID NO: 24)

Clone: 1-G10

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCCGCTATTAGTGGTAGTGGTAACACATACTATGCA
GACTCCGTGAAGGGCCGGTTCACCATCTCCAGAGACAATTCCAAGAACACGCTGTATCTG
CAAATGAACAGCCTGAGAGCCGAGGACACTGCCGTGTATTACTGTGCGAGAGCCTCCCAC
CGTATATTAGGTTATGCTTTTGATATCTGGGGCCAGGGTACACTGGTCACCGTGAGCTCA (SEQ ID NO: 25)

Variable light region (V<sub>L</sub>)
CAGTCTGTGCTGACTCAGCCACCCTCAGCGTCTGGGACCCCCGGGCAGAGGGTCACCATC
TCTTGTTCTGGAAGCCGCTCCAACATCGGGAGAAATGCTGTTAGTTGGTATCAGCAGCTC
CCAGGAACGGCCCCCAAACTCCTCATCTATGCTAACAGCAATCGGCCCTCAGGGGTCCCT
GACCGATTCTCTGGCTCCAAGTCTGGCACCTCAGCCTCCTGGCCATCAGTGGGCTCCGG
TCCGAGGATGAGGCTGATTATTACTGTGCAGCATGGGATGGCAGCCTGAATGGTTGGGTG
TTCGGCGGAGGAACCAAGCTGACGGTCC (SEQ ID NO:26)

Clone: 2-D03

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCAAGTATTAGTGTTGGTGGACATAGGACATATTAT
GCAGATTCCGTGAAGGGCCGGTCCACCATCTCCAGAGACAATTCCAAGAACACGCTGTAT
CTGCAAATGAACAGCCTGAGAGCCGAGGACACTGCCGTGTATTACTGTGCACGGATACGG
GTGGGTCCGTCCGGCGGGGCCTTTGACTACTGGGGCCAGGGTACACTGGTCACCGTGAGC
TCA (SEQ ID NO:27)

Variable light region (V<sub>L</sub>)
CAGTCTGTGCTGACTCAGCCACCCTCAGCGTCTGGGACCCCCGGGCAGAGGGTCACCAT
CTCCTGCTCTGGAAGCAACACCAACATTGGGAAGAACTATGTATCTTGGTATCAGCAGC
TCCCAGGAACGGCCCCCAAACTCCTCATCTATGCTAATAGCAATCGGCCCTCAGGGGTC
CCTGACCGATTCTCTGGCTCCAAGTCTGGCACCTCAGCCTCCTGGCCATCAGTGGGCT
CCGGTCCGAGGATGAGGCTGATTATTACTGTGCGTCATGGGATGCCAGCCTGAATGGTT
GGGTATTCGGCGGAGGAACCAAGCTGACGGTCCTAGGT (SEQ ID NO: 28)

Clone: 2-F07

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATCCACCATCTCCAGAGACAATTCCAAGAACACGCTGTAT
CTGCAAATGAACAGCCTGAGAGCCGAGGACACTGCCGTGTATTACTGTGCGAGGCTCACA
AATATTTTGACTGGTTATTATACCTCAGGATATGCTTTTGATATCTGGGGCCAAGGTACA
CTGGTCACCGTGAGCTCA (SEQ ID NO: 29)

Variable light region (V<sub>L</sub>)
CAGTCTGTGCTGACTCAGCCACCCTCAGCGTCTGGGACCCCCGGGCAGAGGGTCACCATC
TCCTGCTCTGGAAGCACCTCCAACATTGGGAAGAATTATGTATCCTGGTATCAGCAGCTC
CCAGGAACGGCCCCCAAACTCCTCATCTATGGTAACAGCAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGCCAGCCTCAGTGGTTGGGTG
TTCGGCGGAGGAACCAAGCTGACGGTCCTAGGT (SEQ ID NO: 30)

Clone: 2-F09

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTCAGTAGTTCTTGGATGAGTTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAGTAGGG
AACTACGGTTTCTACCACTACATGGACGTCTGGGGCCAAGGTACACTGGTCACCGTGAGC
TCA (SEQ ID NO: 31)

Variable light region (V<sub>L</sub>)
CAGTCTGTGCTGACTCAGCCACCCTCAGCGTCTGGGACCCCCGGGCAGAGGGTCACCATC
TCTTGTTCTGGAGGCAGCTCAAACATCGGAAAAGAGGTGTAAATTGGTATCAGCAGCTC
CCAGGAACGGCCCCCAAACTCCTCATCTATGGTAACAGAAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCTACATGGATTACAGCCTCAATGCTTGGGTG
TTCGGCGGAGGAACCAAGCTGACGGTCCTAGGT (SEQ ID NO: 32)

Clone: 4-A02

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTTAGTAGCTATTGGATGAGCTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAATTAAA
CGGTTACGATTCGGCTGGACCCCTTTTGACTACTGGGGCCAGGGTACACTGGTCACCGTG
AGCTCA (SEQ ID NO: 33)

Variable light region (V<sub>L</sub>)
CAGTCTGTTCTGACTCAGCCACCCTCAGCGTCTGGGACCCCCGGGCAGAGGGTCACCATC
TCCTGTTCTGGAAGCAGCTCCAACATCGGAAATAATGGTGTAAACTGGTATCAGCAGCTC
CCAGGAACGGCCCCCAAACTCCTCATCTATGGTAACAACAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGCGTGGTTGGCTG
TTCGGCGGAGGAACCAAGCTGACGGTCCTAGGT (SEQ ID NO: 34)

Clone. 4-C03

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCATCCATTAGTAGTAGTAGTAGTTACATATACTAC
GCAGACTCAGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAGTCAAT
AGCAAAAAGTGGTATGAGGGCTACTTCTTTGACTACTGGGGCCAGGGTACACTGGTCACC
GTGAGCTCA (SEQ ID NO: 35)

Variable light region (V<sub>L</sub>)
CAGTCTGTGCTGACTCAGCCACCCTCAGCGTCTGGGACCCCCGGGCAGAGGGTCACCATC
TCCTGCTCTGGAAGCAGCTCCAACATTGGGAATAATTATGTATCCTGGTATCAGCAGCTC
CCAGGAACGGCCCCCAAACTCCTCATCTATGGTAACAGCAATCGGCCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGTCTGAGTGGTTGGGTG
TTCGGCGGAGGAACCAAGCTGACGGTCCTAGGT (SEQ ID NO: 36)

Clone: 4-D04

Variable heavy (V<sub>H</sub>) region
GAGGTGCAGCTGTTGGAGTCTGGGGGAGGCTTGGTACAGCCTGGGGGGTCCCTGAGACTC
TCCTGTGCAGCCTCTGGATTCACCTTCAGTAACGCCTGGATGAGCTGGGTCCGCCAGGCT
CCAGGGAAGGGGCTGGAGTGGGTCTCATCCATTAGTACTAGTAGTAATTACATATACTAC
GCAGACTCAGTGAAGGGCCGGTTCACCATCTCCAGAGACAATTCCAAGAACACGCTGTAT
CTGCAAATGAACAGCCTGAGAGCCGAGGACACTGCCGTGTATTACTGTGCGAGAGTCAAG
AAGTATAGCAGTGGCTGGTACTCGAATTATGCTTTTGATATCTGGGGCCAAGGTACACTG
GTCACCGTGAGCTCA (SEQ ID NO: 37)

Variable light region (V<sub>L</sub>)
CAGTCTGTGCTGACTCAGCCACCCTCAGCGTCTGGGACCCCCGGGCAGAGGGTCACCATC
TCCTGCTCTGGAAGCAGCTCCAGCATTGGGAATAATTTTGTATCCTGGTATCAGCAGCTC
CCAGGAACGGCCCCCAAACTCCTCATCTATGACAATAATAAGCGACCCTCAGGGGTCCCT
GACCGATTCTCTGGCTCCAAGTCTGGCACCTCAGCCTCCCTGGCCATCAGTGGGCTCCGG
TCCGAGGATGAGGCTGATTATTACTGTGCAGCATGGGATGACAGCCTGAATGGTTGGGTG
TTCGGCGGAGGAACCAAGCTGACGGTCCTAGGT (SEQ ID NO: 38)

Light Chain Vector

Heavy Chain vector

This graph shows the result from 25 ng purified IgG detected with rabbit-anti-Human IgG-HRP (DAKO P214) and luminescence at 700nm. The plate was coated with 0.5 µg LDL/well.

PEPTIDE-BASED PASSIVE IMMUNIZATION THERAPY FOR TREATMENT OF ATHEROSCLEROSIS

PRIORITY INFORMATION

This application is a divisional of U.S. patent application Ser. No. 10/679,032 filed on Oct. 3, 2003, now U.S. Pat. No. 7,468,183 issued on Dec. 23, 2008, which claims priority to U.S. Provisional Patent Appln. No. 60/421,067, filed Oct. 25, 2002, Swedish Patent Application No. 0302312-4, filed Aug. 27, 2003 and Swedish Patent Application No. 0202959-3, filed Oct. 4, 2002 all of which are incorporated herein in their entirety.

BACKGROUND OF THE INVENTION

1. Field of Invention

The present invention relates to new recombinant human antibodies raised against peptides being derivatives of apolipoprotein B, in particular antibodies to be used for immunization therapy for treatment of atherosclerosis, method for their preparation, and method for passive immunization using said antibodies.

In Particular the Invention Includes:

The use of any isolated recombinant antibody raised against an oxidized form of the peptides listed in table 1, in particular MDA-modified peptides, preferably together with a suitable carrier and adjuvant as an immunotherapy or "anti-atherosclerosis "vaccine" for prevention and treatment of ischemic cardiovascular disease.

2. Description of the Prior Art

The protective effects of humoral immunity are known to be mediated by a family of structurally related glycoproteins called antibodies. Antibodies initiate their biological activity by binding to antigens. Antibody binding to antigens is generally specific for one antigen and the binding is usually of high affinity. Antibodies are produced by B-lymphocytes. Blood contains many different antibodies, each derived from a clone of B-cells and each having a distinct structure and specificity for antigen. Antibodies are present on the surface of B-lymphocytes, in the plasma, in interstitial fluid of the tissues and in secretory fluids such as saliva and mucous on mucosal surfaces.

All antibodies are similar in their overall structure, accounting for certain similarities in physico-chemical features such as charge and solubility. All antibodies have a common core structure of two identical light chains, each about 24 kilodaltons, and two identical heavy chains of about 55-70 kilodaltons each. One light chain is attached to each heavy chain, and the two heavy chains are attached to each other. Both the light and heavy chains contain a series of repeating homologous units, each of about 110 amino acid residues in length which fold independently in a common globular motif, called an immunoglobulin (Ig) domain. The region of an antibody formed by the association of the two heavy chains is hydrophobic. Antibodies, and especially monoclonal antibodies, are known to cleave at the site where the light chain attaches to the heavy chain when they are subjected to adverse physical or chemical conditions. Because antibodies contain numerous cysteine residues, they have many cysteine-cysteine disulfide bonds. All Ig domains contain two layers of beta-pleated sheets with three or four strands of anti-parallel polypeptide chains.

Despite their overall similarity, antibody molecules can be divided into a small number of distinct classes and subclasses based on physicochemical characteristics such as size, charge and solubility, and on their behavior in binding to antigens. In humans, the classes of antibody molecules are: IgA, IgD, IgE, IgG and IgM. Members of each class are said to be of the same isotype. IgA and IgG isotypes are further subdivided into subtypes called IgA1, IgA2 and IgG1, IgG2, IgG3 and IgG4. The heavy chains of all antibodies in an isotype share extensive regions of amino acid sequence identity, but differ from antibodies belonging to other isotypes or subtypes. Heavy chains are designated by the letters of the Greek alphabet corresponding to the overall isotype of the antibody, e.g., IgA contains .alpha., IgD contains .delta., IgE contains .epsilon., IgG contains .gamma., and IgM contains .mu. heavy chains. IgG, IgE and IgD circulate as monomers, whereas secreted forms of IgA and IgM are dimers or pentamers, respectively, stabilized by the J chain. Some IgA molecules exist as monomers or trimers.

There are between $10^8$ and $10^{10}$ structurally different antibody molecules in every individual, each with a unique amino acid sequence in their antigen combining sites. Sequence diversity in antibodies is predominantly found in three short stretches within the amino terminal domains of the heavy and light chains called variable (V) regions, to distinguish them from the more conserved constant (C) regions.

Atherosclerosis is a chronic disease that causes a thickening of the innermost layer (the intima) of large and medium-sized arteries. It decreases blood flow and may cause ischemia and tissue destruction in organs supplied by the affected vessel. Atherosclerosis is the major cause of cardiovascular disease including myocardial infarction, stroke and peripheral artery disease. It is the major cause of death in the western world and is predicted to become the leading cause of death in the entire world within two decades.

The disease is initiated by accumulation of lipoproteins, primarily low-density lipoprotein (LDL), in the extracellular matrix of the vessel. These LDL particles aggregate and undergo oxidative modification. Oxidized LDL is toxic and cause vascular injury. Atherosclerosis represents in many respects a response to this injury including inflammation and fibrosis.

In 1989 Palinski and coworkers identified circulating autoantibodies against oxidized LDL in humans. This observation suggested that atherosclerosis may be an autoimmune disease caused by immune reactions against oxidized lipoproteins. At this time several laboratories began searching for associations between antibody titers against oxidized LDL and cardiovascular disease. However, the picture that emerged from these studies was far from clear. Antibodies existed against a large number of different epitopes in oxidized LDL, but the structure of these epitopes was unknown. The term "oxidized LDL antibodies" thus referred to an unknown mixture of different antibodies rather than to one specific antibody. T cell-independent IgM antibodies were more frequent than T-cell dependent IgG antibodies.

Antibodies against oxidized LDL were present in both patients with cardiovascular disease and in healthy controls. Although some early studies reported associations between oxidized LDL antibody titers and cardiovascular disease, others were unable to find such associations. A major weakness of these studies was that the ELISA tests used to determine antibody titers used oxidized LDL particles as ligand. LDL composition is different in different individuals, the degree of oxidative modification is difficult both to control and assess and levels of antibodies against the different epitopes in the oxidized LDL particles can not be determined. To some extent, due to the technical problems it has been difficult to evaluate the role of antibody responses against oxidized LDL using the techniques available so far, but, however, it is not possible to create well defined and reproducible components of a vaccine if one should use intact oxidized LDL particles.

Another way to investigate the possibility that autoimmune reactions against oxidized LDL in the vascular wall play a key role in the development of atherosclerosis is to immunize animals against its own oxidized LDL. The idea behind this approach is that if autoimmune reactions against oxidized LDL are reinforced using classical immunization techniques this would result in increased vascular inflammation and progressive of atherosclerosis. To test this hypothesis rabbits were immunized with homologous oxidized LDL and then induced atherosclerosis by feeding the animals a high-cholesterol diet for 3 months.

However, in contrast to the original hypothesis immunization with oxidized LDL had a protective effect reducing atherosclerosis with about 50%. Similar results were also obtained in a subsequent study in which the high-cholesterol diet was combined with vascular balloon-injury to produce a more aggressive plaque development. In parallel with our studies several other laboratories reported similar observations. Taken together the available data clearly demonstrates that there exist immune reactions that protect against the development of atherosclerosis and that these involves autoimmunity against oxidized LDL.

These observations also suggest the possibility of developing an immune therapy or "vaccine" for treatment of atherosclerosis-based cardiovascular disease in man. One approach to do this would be to immunize an individual with his own LDL after it has been oxidized by exposure to for example copper. However, this approach is complicated by the fact that it is not known which structure in oxidized LDL that is responsible for inducing the protective immunity and if oxidized LDL also may contain epitopes that may give rise to adverse immune reactions.

The identification of epitopes in oxidized LDL is important for several aspects:

First, one or several of these epitopes are likely to be responsible for activating the anti-atherogenic immune response observed in animals immunized with oxidized LDL. Peptides containing these epitopes may therefore represent a possibility for development of an immune therapy or "atherosclerosis vaccine" in man. Further, they can be used for therapeutic treatment of atherosclerosis developed in man.

Secondly, peptides containing the identified epitopes can be used to develop ELISAs able to detect antibodies against specific structure in oxidized LDL. Such ELISAs would be more precise and reliable than ones presently available using oxidized LDL particles as antigen. It would also allow the analyses of immune responses against different epitopes in oxidized LDL associated with cardiovascular disease.

U.S. Pat. No. 5,972,890 relates to a use of peptides for diagnosing atherosclerosis. The technique presented in said U.S. patent is as a principle a form of radiophysical diagnosis. A peptide sequence is radioactively labelled and is injected into the bloodstream. If this peptide sequence should be identical with sequences present in apolipoprotein B it will bind to the tissue where there are receptors present for apolipoprotein B. In vessels this is above all atherosclerotic plaque. The concentration of radioactivity in the wall of the vessel can then be determined e.g., by means of a gamma camera. The technique is thus a radiophysical diagnostic method based on that radioactively labelled peptide sequences will bound to their normal tissue receptors present in atherosclerotic plaque and are detected using an external radioactivity analysis. It is a direct analysis method to identify atherosclerotic plaque. It requires that the patient be given radioactive compounds.

Published studies (Palinski et al., 1995, and George et al., 1998) have shown that immunisation against oxidised LDL reduces the development of atherosclerosis. This would indicate that immuno reactions against oxidised LDL in general have a protecting effect. The results given herein have, however, surprisingly shown that this is not always the case. E.g., immunisation using a mixture of peptides #10, 45, 154, 199, and 240 gave rise to an increase of the development of atherosclerosis. Immunisation using other peptide sequences, e.g., peptide sequences #1, and 30 to 34 lacks total effect on the development of atherosclerosis. The results are surprising because they provide basis for the fact that immuno reactions against oxidised LDL, can protect against the development, contribute to the development of atherosclerosis, and be without any effect at all depending on which structures in oxidised LDL they are directed to. These findings make it possible to develop immunisation methods, which isolate the activation of protecting immuno reactions. Further, they show that immunisation using intact oxidised LDL could have a detrimental effect if the particles used contain a high level of structures that give rise to atherogenic immuno reactions.

SUMMARY OF THE INVENTION

The technique of the present invention is based on quite different principles and methods. In accordance with claim 1 the invention relates to antibodies raised against oxidized fragments of apolipoprotein B, which antibodies are used for immunisation against cardiovascular disease.

As an alternative to active immunisation, using the identified peptides described above, passive immunisation with pre-made antibodies directed to the same peptides is an attractive possibility. Such antibodies may be given desired properties concerning e.g. specificity and crossreactivity, isotype, affinity and plasma half-life. The possibility to develop antibodies with predetermined properties became apparent already with the advent of the monoclonal antibody technology (Milstein and Köhler, 1975 Nature, 256:495-7). This technology used murine hybridoma cells producing large amounts of identical, but murine, antibodies. In fact, a large number of preclinical, and also clinical trials were started using murine monoclonal antibodies for treatment of e.g. cancers. However, due to the fact that the antibodies were of non-human origin the immune system of the patients recognised them as foreign and developed antibodies to them. As a consequence the efficacy and plasma half-lives of the murine antibodies were decreased, and often side effects from allergic reactions, caused by the foreign antibody, prevented successful treatment.

To solve these problems several approaches to reduce the murine component of the specific and potentially therapeutic antibody were taken. The first approach comprised technology to make so called chimearic antibodies where the murine variable domains of the antibody were transferred to human constant regions resulting in an antibody that was mainly human (Neuberger et al. 1985, Nature 314:268-70). A further refinement of this approach was to develop humanised antibodies where the regions of the murine antibody that contacted the antigen, the so called Complementarity Determining Regions (CDRs) were transferred to a human antibody framework. Such antibodies are almost completely human and seldom cause any harmful antibody responses when administered to patients. Several chimearic or humanised antibodies have been registered as therapeutic drugs and are now widely used within various indications (Borrebaeck and Carlsson, 2001, Curr. Opin. Pharmacol. 1:404-408).

Today also completely human antibodies may be produced using recombinant technologies. Typically large libraries comprising billions of different antibodies are used. In contrast to the previous technologies employing chimerisation or humanisation of e.g. murine antibodies this technology does not rely on immunisation of animals to generate the specific antibody. In stead the recombinant libraries comprise a huge number of pre-made antibody variants why it is likely that the library will have at least one antibody specific for any antigen. Thus, using such libraries the problem becomes the one to find the specific binder already existing in the library, and not to generate it through immunisations. In order to find the good binder in a library in an efficient manner, various systems where phenotype i.e. the antibody or antibody fragment is linked to its genotype i.e. the encoding gene have been devised. The most commonly used such system is the so called phage display system where antibody fragments are expressed, displayed, as fusions with phage coat proteins on the surface of filamentous phage particles, while simultaneously carrying the genetic information encoding the displayed molecule (McCafferty et al., 1990, Nature 348:552-554). Phage displaying antibody fragments specific for a particular antigen may be selected through binding to the antigen in question. Isolated phage may then be amplified and the gene encoding the selected antibody variable domains may optionally be transferred to other antibody formats as e.g. full length immunoglobulin and expressed in high amounts using appropriate vectors and host cells well known in the art.

The format of displayed antibody specificities on phage particles may differ. The most commonly used formats are Fab (Griffiths et al., 1994. EMBO J. 13:3245-3260) and single chain (scFv) (Hoogenboom et al., 1992, J Mol. Biol. 227:381-388) both comprising the variable antigen binding domains of antibodies. The single chain format is composed of a variable heavy domain (VH) linked to a variable light domain (VL) via a flexible linker (U.S. Pat. No. 4,946,778). Before use as analytical reagents, or therapeutic agents, the displayed antibody specificity is transferred to a soluble format e.g. Fab or scFv and analysed as such. In later steps the antibody fragment identified to have desirable characteristics may be transferred into yet other formats such as full length antibodies.

Recently a novel technology for generation of variability in antibody libraries was presented (WO98/32845, Soderlind et al., 2000, Nature BioTechnol. 18:852-856). Antibody fragments derived from this library all have the same framework regions and only differ in their CDRs. Since the framework regions are of germline sequence the immunogenicity of antibodies derived from the library, or similar libraries produced using the same technology, are expected to be particularly low (Soderlind et al., 2000, Nature BioTechnol. 18:852-856). This property is expected to be of great value for therapeutic antibodies reducing the risk for the patient to form antibodies to the administered antibody thereby reducing risks for allergic reactions, the occurrence of blocking antibodies, and allowing a long plasma half-life of the antibody. Several antibodies derived from recombinant libraries have now reached into the clinic and are expected to provide therapeutic drugs in the near future.

Thus, when met with the challenge to develop therapeutic antibodies to be used in humans the art teaches away from the earlier hybridoma technology and towards use of modern recombinant library technology (Soderlind et al., 2001, Comb. Chem. & High Throughput Screen. 4:409-416). It was realised that the peptides identified (PCT/SE02/00679), and being a integral part of this invention, could be used as antigens for generation of fully human antibodies with predetermined properties. In contrast to earlier art (U.S. Pat. No. 6,225,070) the antigenic structures i.e. the peptides used in the present invention were identified as being particularly relevant as target sequences for therapeutic antibodies (PCT/SE02/00679). Also, in the present invention the antibodies are derived from antibody libraries omitting the need for immunisation of lipoprotein deficient mice to raise murine antibodies (U.S. Pat. No. 6,225,070). Moreover, the resulting antibodies are fully human and are not expected to generate any undesired immunological reaction when administered into patients.

The peptides used, and previously identified (PCT/SE02/00679) are the following:

TABLE 1

| A. High IgG, MDA-difference | | |
|---|---|---|
| P 11. | FLDTVYGNCSTHFTVKTRKG | (SEQ. ID NO: 39) |
| P 25. | PQCSTHILQWLKRVHANPLL | (SEQ. ID NO: 40) |
| P 74. | VISIPRLQAEARSEILAHWS | (SEQ. ID NO: 41) |
| B. High IgM, no MDA-difference | | |
| P 40. | KLVKEALKESQLPTVMDFRK | (SEQ. ID NO: 42) |
| P 68. | LKFVTQAEGAKQTEATMTFK | (SEQ. ID NO: 43) |
| P 94. | DGSLRHKFLDSNIKFSHVEK | (SEQ. ID NO: 44) |
| P 99. | KGTYGLSCQRDPNTGRLNGE | (SEQ. ID NO: 45) |
| P 100. | RLNGESNLRFNSSYLQGTNQ | (SEQ. ID NO: 46) |
| P 102. | SLTSTSDLQSGIIKNTASLK | (SEQ. ID NO: 47) |
| P 103. | TASLKYENYELTLKSDTNGK | (SEQ. ID NO: 48) |
| P 105. | DMTFSKQNALLRSEYQADYE | (SEQ. ID NO: 49) |
| P 177. | MKVKIIRTIDQMQNSELQWP | (SEQ. ID NO: 50) |
| C. High IgG, no MDA difference | | |
| P 143. | IALDDAKINFNEKLSQLQTY | (SEQ. ID NO: 51) |
| P 210. | KTTKQSFDLSVKAQYKKNKH | (SEQ. ID NO: 52) |
| D. NHS/AHP, IgG-ak > 2, MDA-difference | | |
| P1. | EEEMLENVSLVCPKDATRFK | (SEQ. ID NO: 53) |
| P 129. | GSTSHHLVSRKSISAALEHK | (SEQ. ID NO: 54) |
| P 148. | IENIDFNKSGSSTASWIQNV | (SEQ. ID NO: 55) |
| P 162. | IREVTQRLNGEIQALELPQK | (SEQ. ID NO: 56) |
| P 252. | EVDVLTKYSQPEDSLIPFFE | (SEQ. ID NO: 57) |
| E. NHS/AHP, IgM-ak > 2, MDA-difference | | |
| P 301. | HTFLIYITELLKKLQSTTVM | (SEQ. ID NO: 58) |
| P 30. | LLDIANYLMEQIQDDCTGDE | (SEQ. ID NO: 59) |
| P 31. | CTGDEDYTYKIKRVIGNMGQ | (SEQ. ID NO: 60) |
| P 32. | GNMGQTMEQLTPELKSSILK | (SEQ. ID NO: 61) |
| P 33. | SSILKCVQSTKPSLMIQKAA | (SEQ. ID NO: 62) |
| P 34. | IQKAAIQALRKMEPKDKDQE | (SEQ. ID NO: 63) |
| P 100. | RLNGESNLRFNSSYLQGTNQ | (SEQ. ID NO: 64) |

TABLE 1-continued

```
P 107.  SLNSHGLELNADILGTDKIN    (SEQ. ID NO: 65)
P 149.  WIQNVDTKYQIRIQIQEKLQ    (SEQ. ID NO: 66)
P 169.  TYISDWWTLAAKNLTDFAEQ    (SEQ. ID NO: 67)
P 236.  EATLQRIYSLWEHSTKNHLQ    (SEQ. ID NO: 68)

F. NHS/AHP, IgG-ak < 0.5, no MDA-difference

P 10.   ALLVPPETEEAKQVLFLDTV    (SEQ. ID NO: 69)
P 45.   IEIGLEGKGFEPTLEALFGK    (SEQ. ID NO: 70)
P 111.  SGASMKLTTNGRFREHNAKF    (SEQ. ID NO: 71)
P 154.  NLIGDFEVAEKINAFRAKVH    (SEQ. ID NO: 72)
P 199.  GHSVLTAKGMALFGEGKAEF    (SEQ. ID NO: 73)
P 222.  FKSSVITLNTNAELFNQSDI    (SEQ. ID NO: 74)
P 240.  FPDLGQEVALNANTKNQKIR    (SEQ. ID NO: 75)
``` or an active site of one or more of these peptides.

In Table 1 above, the following is due:
(A) Fragments that produce high levels of IgG antibodies to MDA-modified peptides (n=3),
(B) Fragments that produce high levels of IgM antibodies, but no difference between native and MDA-modified peptides (n=9),
(C) Fragments that produce high levels of IgG antibodies, but no difference between native and MDA-modified peptides (n=2),
(D) Fragments that produce high levels of IgG antibodies to MDA-modified peptides and at least twice as much antibodies in the NHP-pool as compared to the AHP-pool (n=5),
(E) Fragments that produce high levels of IgM antibodies to MDA-modified peptides and at least twice as much antibodies in the NHP-pool as compared to the AHP-pool (n=11), and
(F) Fragments that produce high levels of IgG antibodies, but no difference between intact and MDA-modified peptides but at least twice as much antibodies in the AHP-pool as compared to the NHP-pool (n=7).

The present invention relates to the use of at least one recombinant human antibody or an antibody fragment thereof directed towards at least one oxidized fragment of apolipoprotein B in the manufacture of a pharmaceutical composition for therapeutical or prophylactical treatment of atherosclerosis by means of passive immunization.

Further the invention relates to the recombinant preparation of such antibodies, as well as the invention relates to method for passive immunization using such antibodies raised using an oxidized apolipoprotein B fragment, as antigen, in particular a fragment as identified above.

The present invention utilises a recombinant antibody fragment library to generate specific human antibody fragments against oxidized, in particular MDA modified peptides derived from Apo B100. Identified antibody fragments with desired characteristics may then rebuilt into full length human immunoglobulin to be used for therapeutic purposes.

BRIEF DESCRIPTION OF THE DRAWINGS

FIGS. 1A-1C are ELISA results from Screen II;
FIGS. 2A-2F are graphs of dose response for ELISAs;
FIG. 3 are the DNA sequences of various regions.

DETAILED DESCRIPTION OF THE INVENTION

Figure 1A:
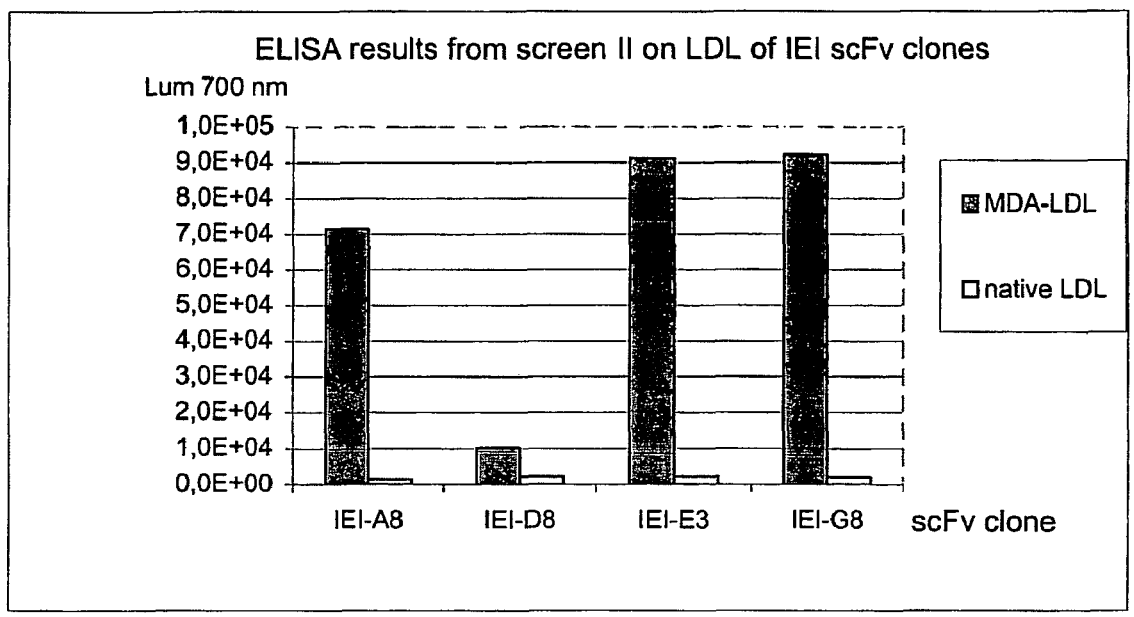

Below will follow a detailed description of the invention exemplified by, but not limited to, human antibodies derived from a recombinant antibody fragment library and directed towards two MDA modified peptides from ApoB 100.

EXAMPLE 1

Selection of scFv Against MDA Modified Peptides
IEIGL EGKGF EPTLE ALFGK (SEQ. ID NO: 70)
(P45, Table 1) and KTTKQ SFDLS VKAQY
KKNKH (SEQ. ID NO: 52) (P210, Table 1)

The target antigens were chemically modified to carry Malone-di-aldehyde (MDA) groups on lysines and histidines. The modified peptides were denoted IEI (P45) and KTT (P210).

Selections were performed using BioInvent's n-CoDeR™scFv library for which the principle of construction and production have been described in Soderlind et al. 2000, Nature BioTechnology. 18, 852-856. The library contains approximately $2 \times 10^{10}$ independent clones and a 2000 fold excess of clones were used as input for each selection. Selections were performed in three rounds. In selection round 1, Immunotubes (NUNC Maxisorb™-444202) were coated with 1.2 ml of 20 □g/ml MDA-modified target peptides in PBS (137 mM NaCl, 2.7 mM KCl, 4.3 mM $Na_2HPO_4$, 1.4 mM $KH_2PO_4$) with end over end agitation at +4° C. over night. The tubes were then blocked with TPBSB5% (5% BSA, 0.05% Tween 20, 0.02% sodium Azide in PBS) for 30 minutes and washed twice with TPBSB3% (3% BSA, 0.05% Tween 20, 0.02% sodium Azide in PBS) before use. Each target tube was then incubated with approximately $2 \times 10^{13}$ CFU phages from the n-CoDeR™ library in 1.8 ml TPBSB3% for 2 h at room temperature, using end over end agitation. The tubes were then washed with 15×3 ml TPBSB3% and 2×1 ml PBS before the bound phages were eluted with 1 ml/tube of 2 mg/ml trypsin (Roche, 109819) for 30 minutes at room temperature. This procedure takes advantage of a specific trypsin site in the scFv-fusion protein to release the phage from the target. The reaction was stopped by the addition of 100 □of Aprotein (0.2 mg/ml, Roche, cat.236624), and the immunotubes were washed with 300 ul PBS, giving a final volume of 1.4 ml.

For amplification of the selected phage E. Coli HB101F' cells were grown exponentially in 10 ml of LB medium (Merck, cat. 1.10285) to $OD_{600}$=0.5 and infected with the selected and eluted phage principally as described (Soderlind et al., 2000, Nature BioTechnol. 18, 852-856. The resulting phage supernatant was then precipitated by addition of ¼ volume of 20% $PEG_{6000}$ in 2.5 M NaCl and incubated for 5 h at +4° C. The phages were then pelleted by centrifugation for 30 minutes, 13000×g, re-suspended in 500 □ PBS and used in selection round 2.

The amplified phagestock was used in selection round 2 in a final volume of 1.5 ml of 5% BSA, 0.05% Tween 20, 0.02% sodium Azide in PBS. Peptide without MDA modification (4×10⁻⁷ M) was also included for competition against binders to MDA-unmodified target peptide. The mixture was incubated in immunotubes prepared with antigen as described above, except that the tubes were blocked with 1% Casein instead of TPBSB3%. The incubations and washing of the immunotubes were as described for selection 1. Bound phages were then eluted for 30 minutes using 600 μl of 100 mM Tris-Glycine buffer, pH 2.2. The tubes were washed with additional 200 μl glycin buffer and the eluates were pooled and then neutralised with 96 μl of 1 M Tris-HCl, pH 8.0. The samples were re-natured for 1 h at room temperature and used for selection round 3.

For selection round 3, BSA, Tween 20 and Sodium Azide were added to the renaturated phage pool to a final concentration of 3%, 0.05% and 0.02%, respectively. Competitor peptides, MDA modified unrelated peptides as well as native target peptides without modification were added to a concentration of 1×10⁻⁷M. The phage mixtures (1100 μl) were added to immunotubes coated with target antigen as described in selection 1 and incubated over night at 4° C. with agitation. The tubes were then washed with 3×3 ml TPBSB 3%, 5×3 ml PBS and eventually bound phages were eluted using trypsin as described in selection round 1 above. Each eluate was infected to 10 ml of logarithmically growing HB101F' in LB containing 100 μg/ml ampicillin, 15 μg/ml tetracycline, 0.1% glucose, and grown over night at 30° C., 200 rpm in a shaker incubator.

The over night cultures were used for mini scale preparation of plasmid DNA, using Biorad mini prepp Kit (Cat. 732 6100). To remove the phage gene III part from the expression vector, 0.25 μg of the plasmid DNA was cut for 2 h at 37° C. using 2.5 U Eag-1 (New England Biolabs, cat. R050) in the buffer recommended by the supplier. The samples were then heat inactivated for 20 minutes at 65° C. and ligated over night at 16° C. using 1 U T4 DNA ligase in 30 μl of 1× ligase buffer (Gibco/BRL). This procedure will join two Eag-1 sites situated on opposite sides of the phage gene III fragment, thus creating a free scFv displaying a terminal 6xhis tag. After ligation the material was digested for 2 h at 37° C. in a solution containing 30 ul ligation mix, 3.6 μl 10×REACT3 stock, 0.4 μl 1 M NaCl, 5 μl H₂O₂, in order to destroy clones in which the phage gene III segment had been religated. Twenty (20) ng of the final product were transformed into chemical competent Top10F' and spread on 500 cm² Q-tray LA-plates (100 μg/ml Amp, 1% glucose), to enable the picking of single colonies for further screening.

Screening of the n-CoDeR™scFv Library for Specific Antibody Fragments Binding T0 MDA Modified Peptides from Apolipoprotein B-100

In order to identify scFv that could discriminate between MDA modified IEI (P45) peptide and native IEI and between MDA modified KTT (P210) and native KTT respectively screenings were performed on bacterial supernatants from selected scFv expressing clones.

Colony picking of single clones, expression of scFv and screening number 1 was performed on BioInvent's automatic system according to standard methods. 1088 and 831 single clones selected against the MDA modified IEI and KTT peptides respectively were picked and cultured and expressed in micro titre plates in 100 μl LB containing 100 μg ampicillin/ml.

For screening number 1 white Assay plates (Greiner 655074) were coated with 54 pmol peptide/well in coating buffer (0.1 M Sodium carbonate, pH 9.5), either with MDA modified peptide which served as positive target or with corresponding unmodified peptide which served as non target. In the ELISA the expressed scFv were detected through a myc-tag situated C-terminal to the scFv using 1 μg/ml of anti-c-myc monoclonal (9E10 Roche 1667 149) in wash buffer. As a secondary antibody Goat-anti-mouse alkaline phosphatase conjugate (Applied Biosystems Cat # AC32ML) was used at 25000 fold dilution. For luminescence detection CDP-Star Ready to use with Emerald II™-Tropix®-(Applied Biosystems Cat # MS100RY) were used according to suppliers recommendation.

Figure 1B:
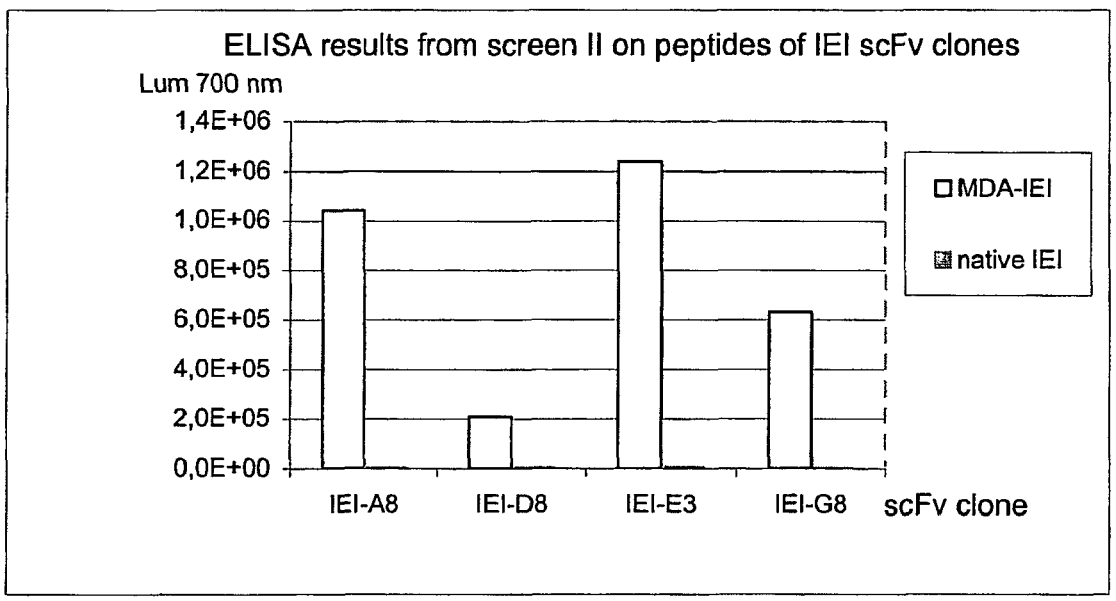

ScFv clones that bound MDA modified peptide but not native peptide were re expressed as described above and to screening another time in a luminescent ELISA (Table 2 and FIG. 1). Tests were run both against directly coated peptides (108 pmol/well coated with PBS) and the more physiological target, LDL particles (1 μg/well coated in PBS+1 mM EDTA) containing the ApoB-100 protein with and without MDA modification were used as targets. Positive clones were those that bound oxidised LDL and MDA modified peptide but not native LDL or peptide. The ELISA was performed as above except that the anti-His antibody (MaB050 RαD) was used as the detection antibody. Twelve IEI clones and 2 KTT clones were found to give more than three fold higher luminescence signal at 700 nm for the MDA modified form than for the native form both for the peptide and LDL.

The identified clones were further tested through titration against a fixed amount (1 μg/well) of MDA LDL and native LDL in order to evaluate the dose response of the scFv (FIG. 2).

TABLE 2

Screening results. The number of clones tested in each screening step for each target. The scored hits in percent are shown within brackets.

| | | Target | |
|---|---|---|---|
| | | IEI | KTT |
| Screening number 1 | Tested Clones | 1088 | 831 |
| | Scored Hits | 64 | 33 |
| | (%) | (5.9%) | (4.0%) |
| Screening number 2 | Tested Clones | 64 | 33 |
| | Scored Hits | 12 | 2 |
| | (%) | (1.1%) | (0.2%) |
| Dose response | Tested Clones | 12 | 2 |
| | Scored Hits | 8 | 2 |
| | (%) | (0.7%) | (0.2%) |

The sequences of the chosen scFv clones were determined in order to find unique clones. Bacterial PCR was performed with the Boeringer Mannheim Expand kit using primers (5'-CCC AGT CAC GAC GTT GTA AAA CG-3') (SEQ. ID NO: 76) and (5'-GAA ACA GCT ATG AAA TAC CTA TTG C-3') (SEQ. ID NO: 77) and a GeneAmp PCR system 9700 (PE Applied system) using the temperature cycling program 94° C. 5 min, 30 cycles of 94° C. 30 s, 52° C. for 30 s and 68° C. for 2 min and finally 5 min at 68 min. The sequencing reaction was performed with the bacterial PCR product (five fold diluted) as template, using Big Dye Terminator mix from PE Applied Biosystems and the GeneAmp PCR system 9700 (PE Applied system) and the temperature cycling program 25 cycles of 96° C. 10 s, 50° C. for 5 s and 60° C. for 4 min. The extension products were purified according to the supplier's instructions and the separation and detection of extension products was done by using a PRISM® 3100 Genetic analyser (PE Applied Biosystems). The sequences were analysed by the in house computer program. From the sequence information homologous clones and clones with inappropriate restriction sites were excluded, leaving six clones for IgG conversion. The DNA sequence of the variable heavy (VH) and variable light (VL) domains of the finally selected clones are shown in FIG. 3.

EXAMPLE 2

Transfer of Genes Encoding the Variable Parts of Selected scFv to Full Length Human IgG1 Vestors Bacteria containing scFv clones to be converted to Ig-format were grown over night in LB supplemented with 100 ☐g/ml ampicillin. Plasmid DNA was prepared from over night cultures using the Quantum Prep, plasmid miniprep kit from Biorad (# 732-6100). The DNA concentration was estimated by measuring absorbance at 260 nm, and the DNA was diluted to a concentration of 2 ng/☐l.

VH and VL from the different scFv-plasmids were PCR amplified in order to supply these segments with restriction sites compatible with the expression vectors (see below). 5' primers contain a BsmI and 3' primers contain a BsiWI restriction enzyme cleavage site (shown in italics). 3' primers also contained a splice donor site (shown in bold).

Primers for Amplification of VH-Segments:

```
5'VH:
                                         (SEQ. ID. NO: 13)
5'-GGTGTGCATTCCGAGGTGCAGCTGTTGGAG

3'VH:
                                         (SEQ. ID. NO: 14)
5'-GACGTACGACTCACCTGAGCTCACGGTGACCAG
```

Primers for Amplification of VL-Segments:

```
5'VL:
                                         (SEQ. ID. NO: 15)
5'-GGTGTGCATTCCCAGTCTGTGCTGACTCAG

3'VL:
                                         (SEQ. ID. NO: 16)
5'-GACGTACGTTCTACTCACCTAGGACCGTCAGCTT
```

PCR was conducted in a total volume of 50 µl, containing 10 ng template DNA, 0.4 ☐M 5' primer, 0.4 ☐M 3' primer and 0.6 mM dNTP (Roche, #1 969 064). The polymerase used was Expand long template PCR system (Roche # 1 759 060), 3.5 upper reaction, together with each of the supplied buffers in 3 separate reactions. Each PCR amplification cycle consisted of a denaturing step at 94° C. for 30 seconds, an annealing step at 55° C. for 30 seconds, and an elongating step at 68° C. for 1.5 minutes. This amplification cycle was repeated 25 times. Each reaction began with a single denaturing step at 94° C. for 2 minutes and ended with a single elongating step at 68° C. for 10 minutes. The existence of PCR product was checked by agarose gel electrophoresis, and reactions containing the same amplified material (from reactions with different buffers) were pooled. The PCR amplification products were subsequently purified by spin column chromatography using S400-HR columns (Amersham-Pharmacia Biotech # 27-5240-01).

Four (4) ☐l of from each pool of PCR products were used for TOPO®-TA cloning (pCR 2.1 TOPO®-, InVitrogen #K4550-01) according to the manufacturers recommendations. Bacterial colonies containing plasmids with inserts were grown over night in LB supplemented with 100 ☐g/ml ampicillin and 20 ☐g/ml kanamycin. Plasmid DNA was prepared from over night cultures using the Quantum Prep, plasmid miniprep kit from Biorad (# 732-6100). Plasmid preparations were purified by spin column chromatography using S400-HR columns (Amersham-Pharmacia Biotech # 27-5240-01). Three plasmids from each individual VH and VL cloning were subjected to sequence analysis using Big-Dye®-Cycle Sequencing (Perkin Elmer Applied Biosystem, # 4303150). The cycle sequencing program consisted of a denaturing step at 96° C. for 10 seconds, an annealing step at 50° C. for 15 seconds, and an elongating step at 60° C. for 4 minutes. This cycle was repeated 25 times. Each reaction began with a single denaturing step at 94° C. for 1 minute. The reactions were performed in a volume of 10 ☐l consisting of 1 ☐M primer 5'-CAGGAAACAGCTATGAC (SEQ. ID NO:78), 3 ☐l plasmid DNA and 4 ☐l Big Dye®-reaction mix. The reactions were precipitated according to the manufacturer's recommendations, and samples were run on a ABI PRISM®-3100 Genetic Analyzer. Sequences were compared to the original scFv sequence using the alignment function of the OMIGA sequence analysis software (Oxford Molecular Ltd).

Plasmids containing VH and VL segments without mutations were restriction enzyme digested. To disrupt the pCR 2.1 TOPO® vector, plasmids were initially digested with DraI (Roche # 1 417 983) at 37° C. for 2 hours. Digestions were heat inactivated at 70° C. for 20 minutes and purified by spin column chromatography using S400-HR columns (Amersham-Pharmacia Biotech # 27-5240-01). The purified DraI digestions were subsequently digested with BsmI (Roche # 1 292 307) and BsiWI (Roche # 1 388 959) at 55° C. over night. Digestions were purified using phenol extraction and precipitation. The precipitated DNA was dissolved in 10 ☐l H$_2$O and used for ligation.

Figures 4, 4A:
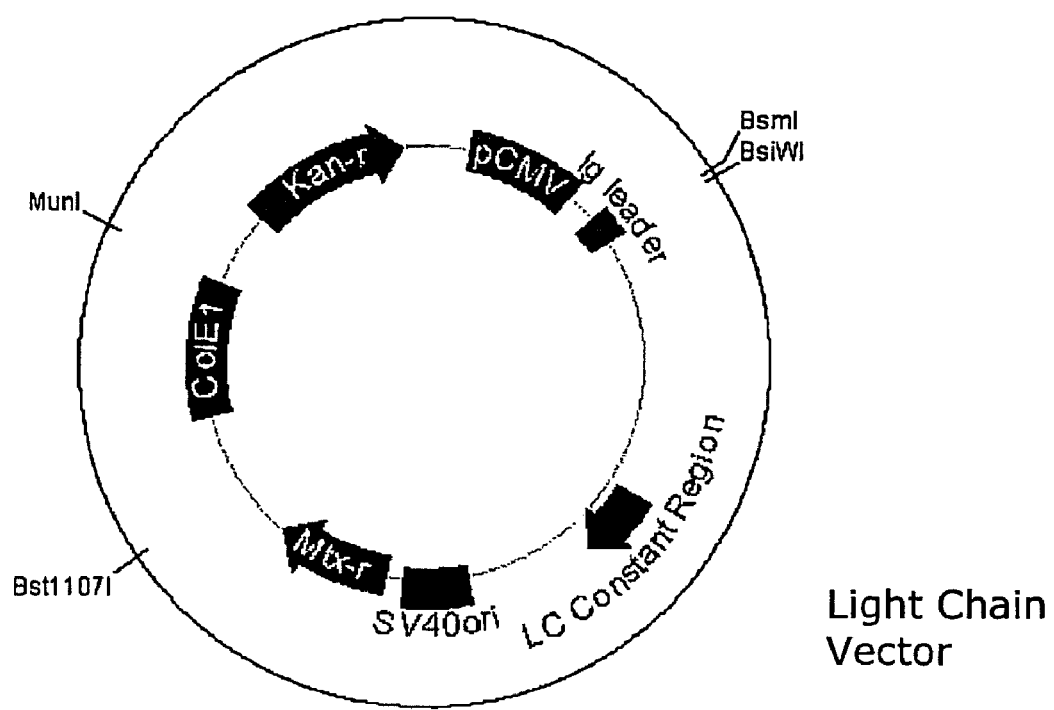
FIGS. 4A and 4B are light and heavy-chain vectors.
Figures 4, 4B:
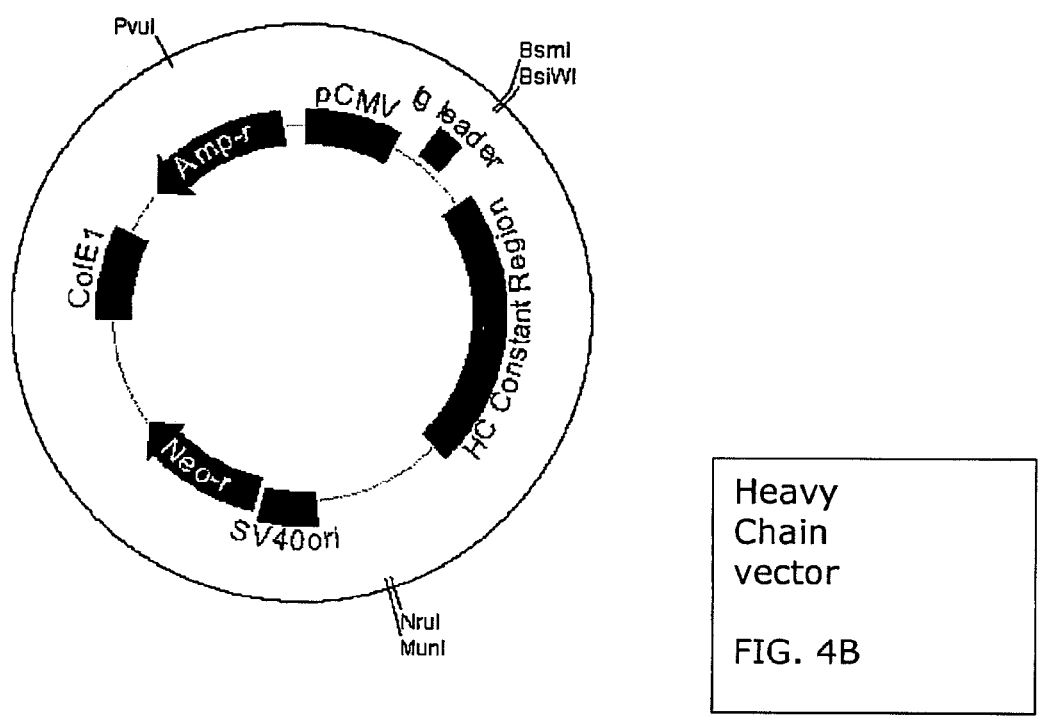

The expression vectors were obtained from Lars Norderhaug (J. Immunol. Meth. 204 (1997) 77-87). After some modifications, the vectors (FIG. 4) contain a CMV promoter, an Ig-leader peptide, a cloning linker containing BsmI and BsiWI restriction sites for cloning of VH/VL, genomic constant regions of IgG1 (heavy chain (HC) vector) or lambda (light chain (LC) vector), neomycin (HC vector) or methotrexate (LC vector) resistance genes for selection in eukaryotic cells, SV40 and ColEI origins of replication and ampicillin (HC vector) or kanamycin (LC vector) resistance genes for selection in bacteria.

The HC and LC vectors were digested with BsmI and BsiWI, phosphatase treated and purified using phenol extraction and precipitation. Ligation were set up at 16° C. over night in a volume of 10 ☐l, containing 100 ng digested vector, 2 ☐l digested VH/VL-pCR 2.1 TOPO®-vector (see above), 1 U T4 DNA ligase (Life Technologies, # 15224-025) and the supplied buffer. 2 ☐l of the ligation mixture were subsequently transformed into 50 ☐l chemocompetent top10F' bacteria, and plated on selective (100 ☐g/ml ampicillin or 20 ☐g/ml kanamycin) agar plates.

Colonies containing HC/LC plasmids with VH/VL inserts were identified by colony PCR:

```
Forward primer:
5'-ATGGGTGACAATGACATC      (SEQ. ID NO: 17)

Reverse primer:
5'-AAGCTTGCTAGCGTACG       (SEQ. ID NO: 18)
```

PCR was conducted in a total volume of 20 ☐l, containing bacterias, 0.5 ☐M forward primer, 0.5 ☐M reverse primer and 0.5 mM dNTP (Roche, #1 969 064). The polymerase used was Expand long template PCR system (Roche # 1 759 060), 0.7 Upper reaction, together with the supplied buffer #3. Each PCR amplification cycle consisted of a denaturing step at 94°

C. for 30 seconds, an annealing step at 52° C. for 30 seconds, and an elongating step at 68° C. for 1.5 minutes. This amplification cycle was repeated 30 times. Each reaction began with a single denaturing step at 94° C. for 2 minutes and ended with a single elongating step at 68° C. for 5 minutes. The existence of PCR product was checked by agarose gel electrophoresis. Colonies containing HC/LC plasmids with VH/VL inserts were grown over night in LB supplemented with 100 µg/ml ampicillin or 20 µg/ml kanamycin. Plasmid DNA was prepared from over night cultures using the Quantum Prep, plasmid miniprep kit from Biorad (# 732-6100). Plasmid preparations were purified by spin column chromatography using S400-HR columns (Amersham-Pharmacia Biotech # 27-5240-01). To confirm the integrity of the DNA sequence, three plasmids from each individual VH and VL were subjected to sequence analysis using Big Dye®-Cycle Sequencing (Perkin Elmer Applied Biosystem, # 4303150). The cycle sequencing program consisted of a denaturing step at 96° C. for 10 seconds, an annealing step at 50° C. for 15 seconds, and an elongating step at 60° C. for 4 minutes. This cycle was repeated 25 times. Each reaction began with a single denaturing step at 94° C. for 1 minute. The reactions were performed in a volume of 10 µl consisting of 1 µM primer (5'-AGACCCAAGCTAGCTTGGTAC) (SEQ. ID NO:79), 3 µl plasmid DNA and 4 µl Big Dye® reaction mix. The reactions were precipitated according to the manufacturer's recommendations, and samples were run on a ABI PRISM® 3100 Genetic Analyzer. Sequences were analysed using the OMIGA sequence analysis software (Oxford Molecular Ltd). The plasmid DNA was used for transient transfection of COS-7 cells (see below) and were digested for production of a joined vector, containing heavy- and light chain genes on the same plasmid.

Heavy and light chain vectors containing VH and VL segments originating from the same scFv were cleaved by restriction enzymes and ligated: HC- and LC-vectors were initially digested with MunI (Roche # 1 441 337) after which digestions were heat inactivated at 70° C. for 20 minutes and purified by spin column chromatography using S200-HR columns (Amersham-Pharmacia Biotech # 27-5120-01). HC-vector digestions were subsequently digested with NruI (Roche # 776 769) and LC-vector digestions with Bst11071 (Roche # 1 378 953). Digestions were then heat inactivated at 70° C. for 20 minutes and purified by spin column chromatography using S400-HR columns (Amersham-Pharmacia Biotech # 27-5240-01). 5 µl of each digested plasmid were ligated at 16° C. over night in a total volume of 20 µl, containing 2 U T4 DNA ligase (Life Technologies, # 15224-025) and the supplied buffer. 2 µl of the ligation mixture were subsequently transformed into 50 µl chemocompetent top10F' bacteria, and plated on selective (100 µg/ml ampicillin and 20 µg/ml kanamycin) agar plates.

Bacterial colonies were grown over night in LB supplemented with 100 µg/ml ampicillin and 20 µg/ml kanamycin. Plasmid DNA was prepared from over night cultures using the Quantum Prep, plasmid miniprep kit from Biorad (# 732-6100). Correctly joined vectors were identified by restriction enzyme digestion followed by analyses of fragment sizes by agarose gel-electrophoreses Plasmid preparations were purified by spin column chromatography using S400-HR columns (Amersham-Pharmacia Biotech # 27-5240-01) and used for transient transfection of COS-7 cells.

COS-7 cells (ATCC # CRL-1651) were cultured at 37° C. with 5% $CO_2$ in Dulbeccos MEM, high glucose+ GlutamaxI™-(Invitrogen # 31966021), supplemented with 0.1 mM non-essential amino acids (Invitrogen # 11140035) and 10% fetal bovine sera (Invitrogen # 12476-024, batch # 1128016). The day before transfection, the cells were plated in 12-well plates (Nunc™-, # 150628) at a density of $1.5 \times 10^5$ cells per well.

Prior to transfection, the plasmid DNA was heated at 70° C. for 15 minutes. Cells were transfected with 1 µg HC-plasmid+1 µg LC-plasmid, or 2 µg joined plasmid per well, using Lipofectamine™-2000 Reagent (Invitrogen, # 11668019) according to the manufacturers recommendations. 24 hours post transfection, cell culture media was changed and the cells were allowed to grow for 5 days. After that, medium was collected and protein production was assayed for using ELISA.

Ninetysix (96)-well plates (Costar # 9018, flat bottom, high binding) were coated at 4° C. over night by adding 100 µl/well rabbit anti-human lamda light chain antibody (DAKO, # A0193) diluted 4000 times in coating buffer (0.1 M sodium carbonate, pH 9.5). Plates were washed 4 times in PBS containing 0.05% Tween 20 and thereafter blocked with 100 µl/well PBS+3% BSA (Albumin, fraction V, Roche # 735108) for 1 h. at room temperature. After washing as above, 100 µl/well of sample were added and incubated in room temperature for 1 hour. As a standard for estimation of concentration, human purified IgG1 (Sigma, # 15029) was used. Samples and standard were diluted in sample buffer (1×PBS containing 2% BSA and 0.5% rabbit serum (Sigma # R4505). Subsequently, plates were washed as described above and 100 µl/well of rabbit anti-human IgG (γ-chain) HRP-conjugated antibody (DAKO, # P214) diluted 8000 times in sample buffer was added and incubated at room temperature for 1 hour. After washing 8 times with PBS containing 0.05% Tween 20, 100 µl/well of a substrate solution containing one OPD tablet (10 mg, Sigma # P8287) dissolved in 15 ml citric acid buffer and 4.5 µl $H_2O_2$ (30%) was added. After 10 minutes, the reaction was terminated by adding 150 µl/well of 1M HCl. Absorbance was measured at 490-650 nm and data was analyzed using the Softmax software.

Bacteria containing correctly joined HC- and LC-vectors were grown over night in 500 ml LB supplemented with ampicillin and kanamycin. Plasmid DNA was prepared from over night cultures using the Quantum Prep, plasmid maxiprep kit from Biorad (# 732-6130). Vectors were linearized using PvuI restriction enzyme (Roche # 650 129). Prior to transfection, the linearized DNA was purified by spin column chromatography using S400-HR columns (Amersham-Pharmacia Biotech # 27-5240-01) and heated at 70° C. for 15 minutes.

EXAMPLE 3

Stable Transfection of NS0 Cells Expressing Antibodies Against MDA Modified Peptides Form Apolipoprotein B-100

NS0 cells (ECACC no. 85110503) were cultured in DMEM (cat nr 31966-021, Invitrogen) supplemented with 10% Fetal Bovine Serum (cat no. 12476-024, lot: 1128016, Invitrogen) and 1×NEAA (non-essential amino acids, cat no. 11140-053, Invitrogen). Cell cultures are maintained at 37° C. with 5% $CO_2$ in humidified environment.

DNA constructs to be transfected were four constructs of IEI specific antibodies (IEI-A8, IEI-D8, IEI-E3, IEI-G8), two of KTT specific antibodies (KTT-B8, KTT-D6) and one control antibody (JFPA12). The day before transfection, the cells were trypsinized and counted, before plating them in a T-75 flask at $12 \times 10^6$ cells/flask. On the day of transfection, when the cells were 85-90% confluent, the cells were plated in 15 ml DMEM+1×NEAA+10% FBS (as above). For each flask of cells to be transfected, 35-40 µg of DNA were diluted into 1.9 ml of OPTI-MEM®-I Reduced Serum Medium (Cat no. 51985-026, lot: 3062314, Invitrogen) without serum. For each flask of cells, 114 µl of Lipofectamine™-2000 Reagent (Cat nr. 11668-019, lot: 1116546, Invitrogen) were diluted into 1.9 ml OPTI-MEM®-I Reduced Serum Medium in another tube and incubated for 5 min at room temperature. The diluted DNA was combined with the diluted Lipofectamine™-2000 Reagent (within 30 min) and incubated at room temperature for 20 min to allow DNA-LF2000 Reagent complexes to form.

The cells were washed with medium once and 11 ml DMEM+1×NEAA+10% FBS were added. The DNA-LF2000 Reagent complexes (3.8 ml) were then added directly to each flask and gently mixed by rocking the flask back and forth. The cells were incubated at 37° C. in a 5% $CO_2$ incubator for 24 h.

The cells were then trypsinized and counted, and subsequently plated in 96-well plates at $2 \times 10^4$ cells/well using five 96-well plates/construct. Cells were plated in 100 ◻l/well of DMEM+1×NEAA+10% FBS (as above) containing G418-sulphate (cat nr.10131-027, lot: 3066651, Invitrogen) at 600 ◻g/ml. The selection pressure was kept unchanged until harvest of the cells.

The cells were grown for 12 days and assayed for antibody production using ELISA. From each construct cells from the 24 wells containing the highest amounts of IgG were transferred to 24-well plates and were allowed to reach confluency. The antibody production from cells in these wells was then assayed with ELISA and 5-21 pools/construct were selected for re-screening (Table 3). Finally cells from the best 1-4 wells for each construct were chosen. These cells were expanded successively in cell culture flasks and finally transferred into triple layer flasks (500 cm2) in 200 ml of (DMEM+1×NEAA+10% Ultra low IgG FBS (cat.no. 16250-078, lot.no. 113466, Invitrogen)+G418 (600 µg/ml)) for antibody production. The cells were incubated for 7-10 days and the supernatants were assayed by ELISA, harvested and sterile filtered for purification.

EXAMPLE 4

Production and Purification of Human IgG1

Supernatants from NSO cells transfected with the different IgG1 antibodies were sterile filtered using a 0.22 µm filter and purified using an affinity medium MabSelect™ with recombinant protein A, (Cat. No. 17519901 Amersham Biosciences).

Bound human IgG1 was eluted with HCL-glycine buffer pH 2.8. The eluate was collected in 0.5 ml fractions and $OD_{280}$ was used to determine presence of protein. The peak fractions were pooled and absorbance was measured at 280 nm and 320 nm. Buffer was changed through dialysis against a large volume of PBS. The presence of endotoxins in the purified IgG-1 preparations was tested using a LAL test (QCL-1000®-, cat. No. 50-647U Bio Whittaker). The samples contained between 1 and 12 EU/ml endotoxin. The purity of the preparations were estimated to exceed 98% by PAGE analysis.

TABLE 3

Summary of Production and Purification of human IgG1

| Clone name | Volume culture supernatant (ml) | Total IgG1 in supernatant (mg) | Total IgG1 Purified (mg) | Yield (%) |
|---|---|---|---|---|
| IEI-A8 | 600 | 68 | 42 | 61.8 |
| IEI-D8 | 700 | 45 | 21 | 46.7 |
| IEI-E3 | 700 | 44.9 | 25.6 | 60 |
| IEI-G8 | 600 | 74 | 42.4 | 57.3 |
| KTT-B8 | 1790 | 77.3 | 37.6 | 48.6 |
| KTT-D6 | 1845 | 47.8 | 31.8 | 66.5 |
| JFPA12 | 2000 | 32.2 | 19.2 | 59.6 |

Figure 5:
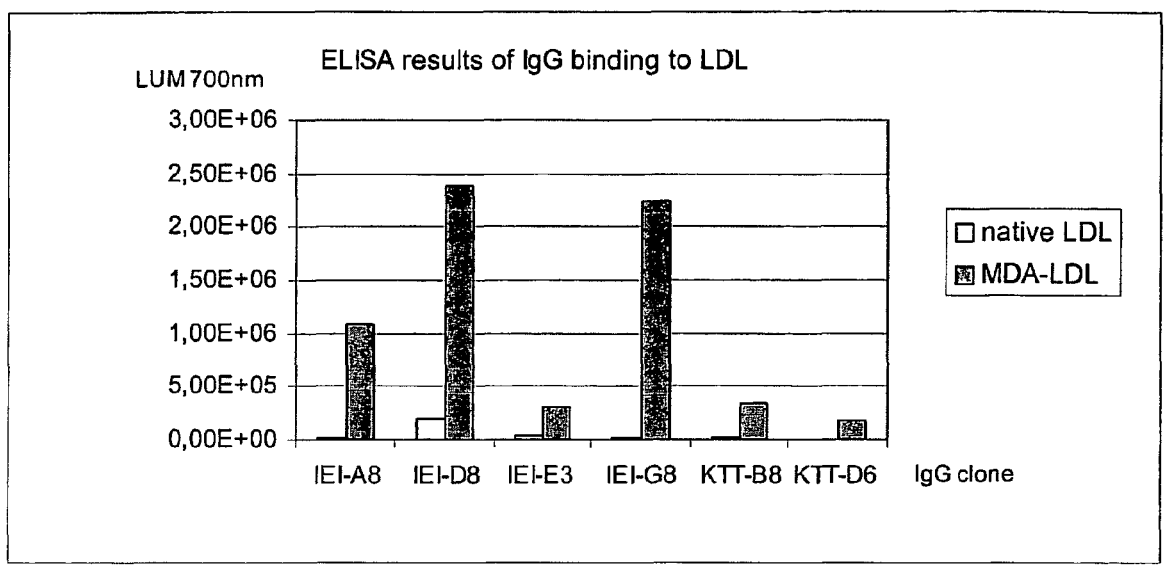
FIG. 5 is a graph of ELISA results.

The purified IgG1 preparations were tested in ELISA for reactivity to MDA modified and unmodified peptides (FIG. 5) and were then used in functional in vitro and in vivo studies.

EXAMPLE 5

Analysis of Possible Anti-Atherogenic Effect of Antibodies are Performed Both in Experimental Animals and in Cell Culture Studies 1. Effect of Antibodies on Atherosclerosis in Apolipoprotein E Knockout (apo E–) Mice.

Five weeks old apo E– mice are fed a cholesterol-rich diet for 15 weeks. This treatment is known to produce a significant amount of atherosclerotic plaques in the aorta and carotid arteries. The mice are then given an intraperitoneal injection containing 500 ◻g of the respective antibody identified above. Control mice are given 500 ◻g of an irrelevant control antibody or PBS alone. Treatments are repeated after 1 and 2 weeks. The mice are sacrificed 4 weeks after the initial antibody injection. The severity of atherosclerosis in the aorta is determined by Oil Red O staining of flat preparations and by determining the size of subvalvular atherosclerotic plaques. Collagen, macrophage and T cell content of subvalvular atherosclerotic plaques is determined by Masson trichrome staining and cell-specific immunohistochemistry. Quantification of Oil Red O staining, the size of the subvalvular plaques, trichrome staining and immunohistochemical staining is done using computer-based image analysis.

Figure 6:
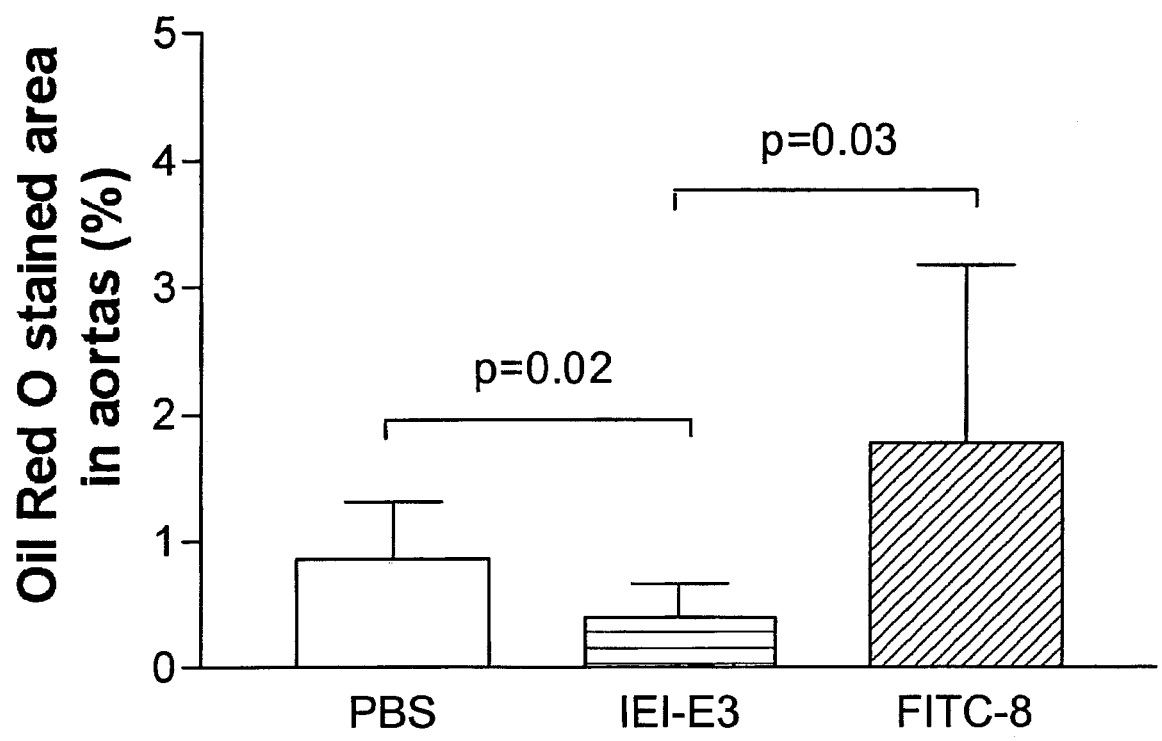
FIG. 6 is a graph of Oil Red 0 Stained area in aortas.

In a first experiment the effect of the antibodies on development of atherosclerosis was analysed in apo E–/– mice fed a high-cholesterol diet. The mice were given three intraperitoneal injections of 0.5 mg antibody with week intervals starting at 21 weeks of age, using PBS as control. They were sacrificed two weeks after the last antibody injection, and the extent of atherosclerosis was assessed by Oil Red O staining of descending aorta flat preparations. A pronounced effect was observed in mice treated with the IEI-E3 antibody, with more than 50% reduction of atherosclerosis as compared to the PBS group (P=0.02) and to a control group receiving a human IgG1 antibody (FITC8) directed against a non-relevant fluorescein isothiocynate (FITC) antigen (P=0.03) (FIG. 6). The mice tolerated the human antibodies well and no effects on the general health status of the mice were evident.

Figure 7:
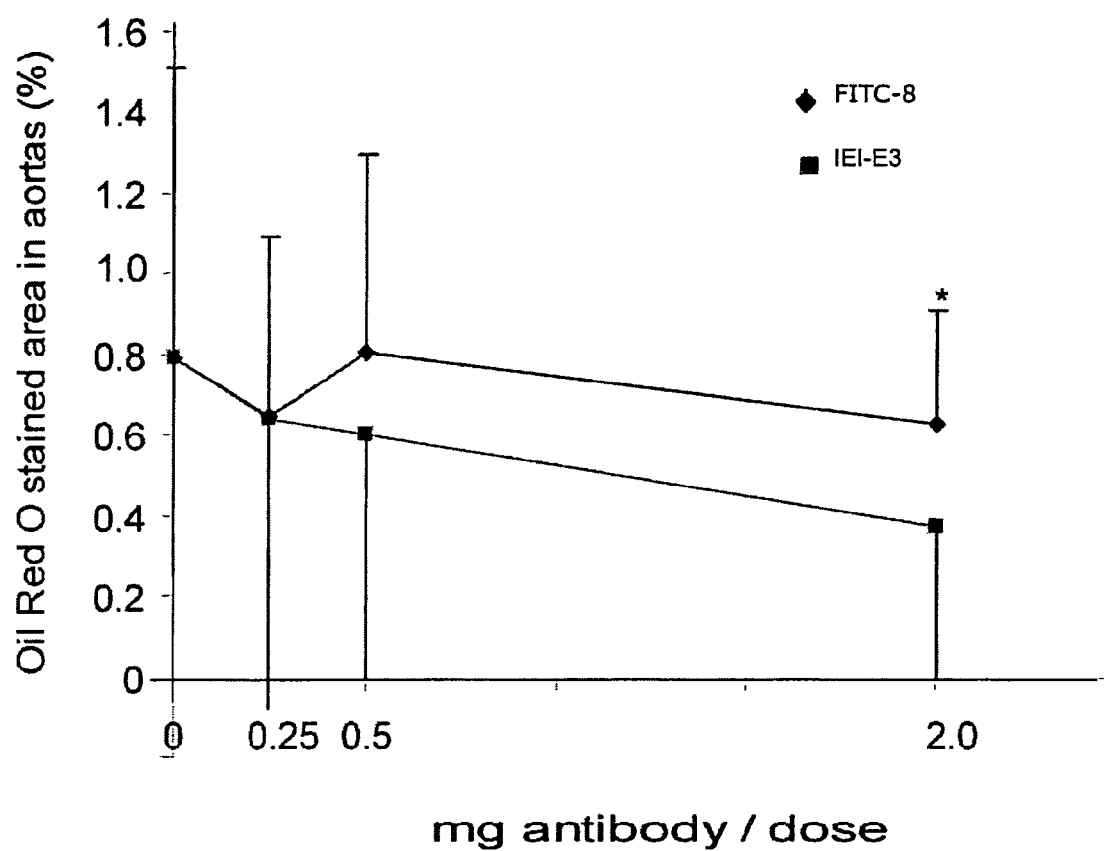
FIG. 7 is a graph of Oil Red 0 stained area in aortas versus antibody product.

To verify the inhibitory effect of the IEI-E3 antibody on development of atherosclerosis we then performed a dose-response study. The schedule was identical to that of the initial study. In mice treated with IEI-E3 antibodies atherosclerosis was reduced by 2% in the 0.25 mg group (n.s.), by 25% in the 0.5 mg group (n.s.) and by 41% (P=0.02) in the 2.0 mg group as compared to the corresponding FITC antibody-treated groups (FIG. 7).

2. Effect of antibodies on neo-intima formation following mechanical injury of carotid arteries in apo E– mice. Mechanical injury of arteries results in development of fibro-muscular neo-intimal plaque within 3 weeks. This plaque resembles morphologically a fibro-muscular atherosclerotic plaque and has been used as one model for studies of the development of raised lesion. Placing a plastic collar around the carotid artery causes the mechanical injury. Five weeks old apo E– mice are fed a cholesterol-rich diet for 14 weeks. The mice are then given an intraperitoneal injection containing 500 μg of the respective antibody. Control mice are given 500 μg of an irrelevant control antibody or PBS alone. The treatment is repeated after 7 days and the surgical placement of the plastic collar is performed 1 day later. A last injection of antibodies or PBS is given 6 days after surgery and the animals are sacrificed 15 days later. The injured carotid artery is fixed, embedded in paraffin and sectioned. The size of the neo-intimal plaque is measured using computer-based image analysis.

3. Effect of Antibodies on Uptake of Oxidized LDL in Cultured Human Macrophages.

Figure 8:
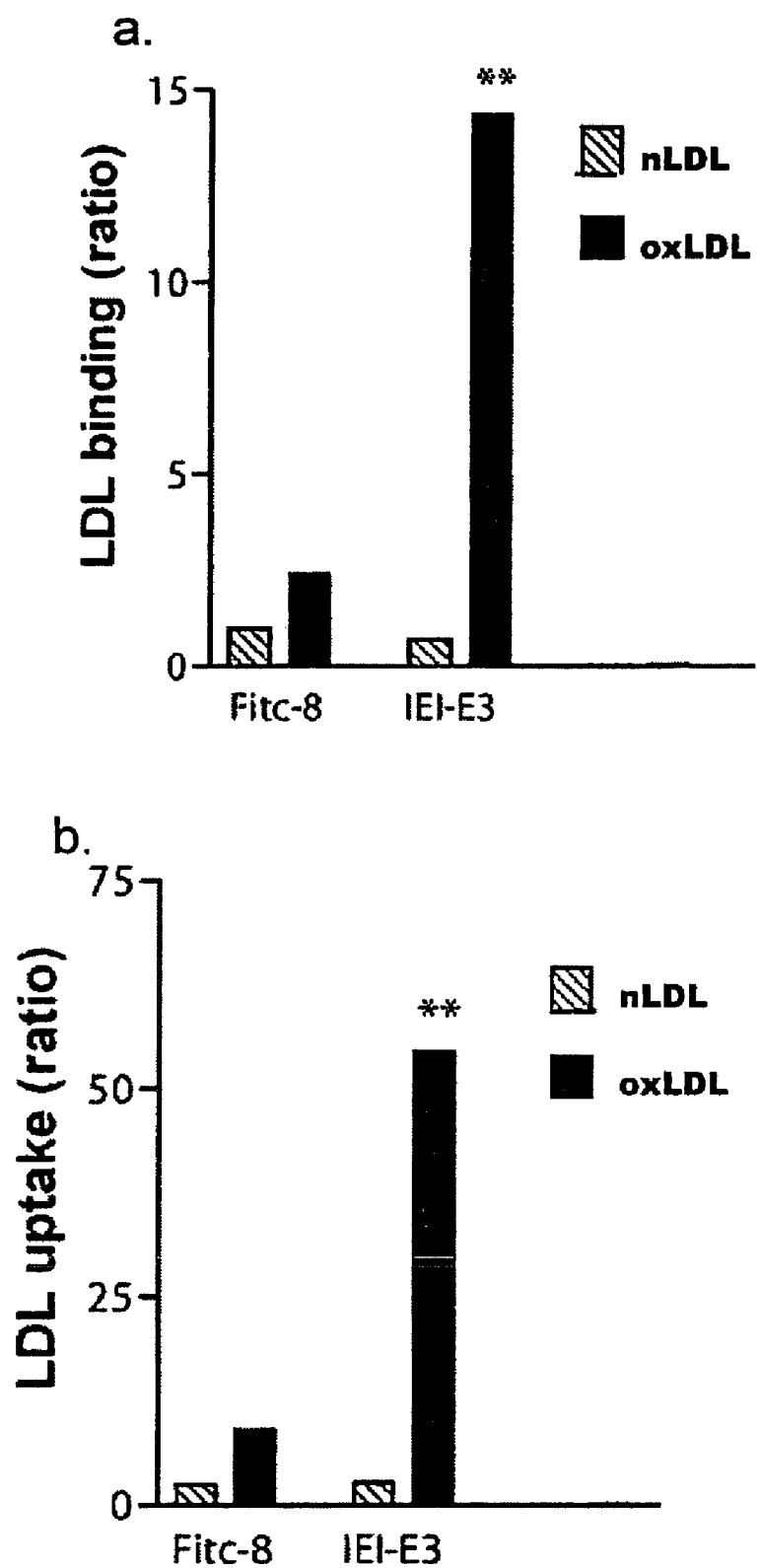
FIGS. 8a and 8b are graphs of LDL uptake.
Figure 9:
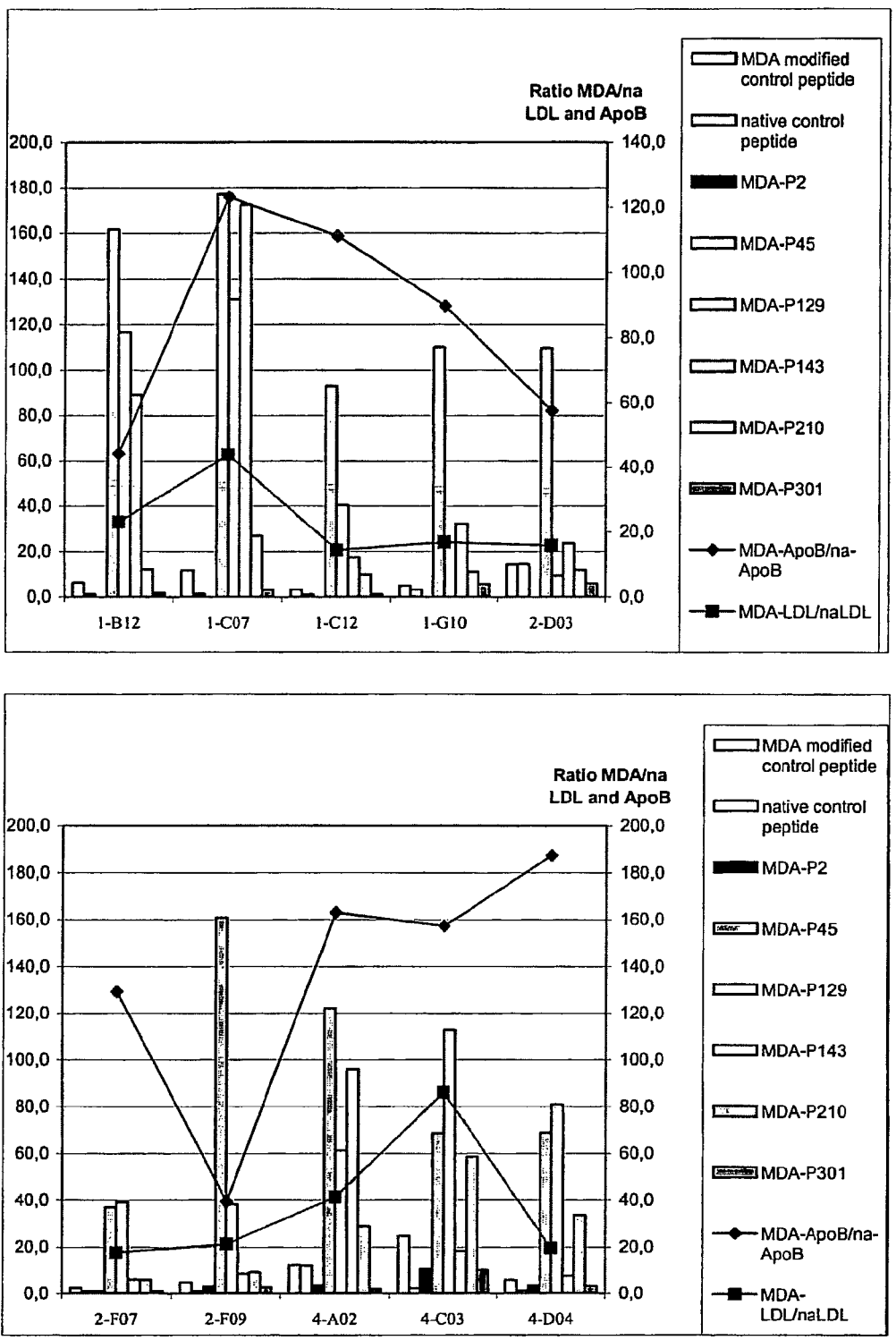
FIG. 9 are graphs of the Ratio MDA/na LDL and ApoB

Uptake of oxidized LDL in arterial macrophages leading to formation of cholesterol-loaded macrophage foam cells is one of the most characteristic features of the atherosclerotic plaque. Several lines of evidence suggest that inhibiting uptake of oxidized LDL in arterial macrophages represent a possible target for treatment of atherosclerosis. To study the effect of antibodies on macrophage uptake of oxidized c are pre-incubated with $^{125}$I-labeled human oxidized LDL for 2 hours. Human macrophages are isolated from blood donor buffy coats by centrifugation in Ficoll hypaque followed by culture in presence of 10% serum for 6 days. The cells are then incubated with medium containing antibody/oxidized LDL complexes for 6 hours, washed and cell-associated radioactivity determined in a gamma-counter. Addition of IEI-E3 antibodies resulted in a five-fold increase in the binding ($P=0.001$) and uptake ($P=0.004$) of oxidized LDL compared to FITC-8 into macrophages, but had no effect on binding or uptake of native LDL (FIGS. 8a and 8b).

4. Effect of antibodies on oxidized LDL-dependent cytotoxicity. Oxidized LDL is highly cytotoxic. It is believed that much of the inflammatory activity in atherosclerotic plaques is explained by cell injury caused by oxidized LDL. Inhibition of oxidized LDL cytotoxicity thus represents another possible target for treatment of atherosclerosis. To study the effect of antibodies on oxidized LDL cytotoxicity cultured human arterial smooth muscle cells are exposed to 100 ng/ml of human oxidized LDL in the presence of increasing concentrations of antibodies (0-200 ng/ml) for 48 hours. The rate of cell injury is determined by measuring the release of the enzyme LDH.

The experiment shown discloses an effect for a particular antibody raised against a particular peptide, but it is evident to the one skilled in the art that all other antibodies raised against the peptides disclosed will behave in the same manner.

The antibodies of the present invention are used in pharmaceutical compositions for passive immunization, whereby the pharmaceutical compositions primarily are intended for injection, comprising a solution, suspension, or emulsion of a single antibody or a mixture of antibodies of the invention in a dosage to provide a therapeutically or prophylactically active level in the body treated. The compositions may be provided with commonly used adjuvants to enhance absorption of the antibody or mixture of antibodies. Other routes of administration may be the nasal route by inhaling the antibody/antibody mixture in combination with inhalable excipients.

Such pharmaceutical compositions may contain the active antibody in an amount of 0.5 to 99.5% by weight, or 5 to 90% by weight, or 10 to 90% by weight, or 25 to 80% by weight, or 40 to 90% by weight.

The daily dosage of the antibody, or a booster dosage shall provide for a therapeutically or prophylactically active level in the body treated to reduce or prevent signs and symptoms of atherosclerosis by way of passive immunization. A dosage of antibody according to the invention may be 1 μg to 1 mg per kg bodyweight, or more.

The antibody composition can be supplemented with other drugs for treating or preventing atherosclerosis or heart-vascular diseases, such as blood pressure lowering drugs, such as beta-receptor blockers, calcium antagonists, diurethics, and other antihypertensive agents.

We claim:

1. Purified or recombinant antibody raised against fragments of apo B100 comprising a variable heavy region ($V_H$) encoded by the nucleic acid sequence consisting of:
   SEQ. ID. NO. 3 in combination with a variable light region ($V_L$) encoded by the nucleic acid sequence consisting of: SEQ. ID. NO. 4.

2. The antibody according to claim 1, wherein the antibody comprises:
   the variable heavy region ($V_H$) encoded by SEQ ID NO: 3
   and the variable light region ($V_L$) encoded by SEQ ID NO: 4.

3. A pharmaceutical composition comprising an isolated human antibody directed towards at least one oxidized fragment of apolipoprotein B for treatment of atherosclerosis by passive immunization, which antibody is present in combination with a pharmaceutical excipient, and wherein said antibody comprises a variable heavy region ($V_H$) which is encoded by SEQ ID NO: 3 and a variable light region ($V_L$) which is encoded by SEQ ID NO: 4.

4. The antibody according to claim 2, wherein the variable heavy region ($V_H$) encoded by SEQ ID NO: 3 and the variable light region ($V_L$) encoded by SEQ ID NO: 4 bind to apolipoprotein peptide sequence of SEQ ID NO:70.

* * * * *

SEQUENCE LISTING

```
<160> NUMBER OF SEQ ID NOS: 79

<210> SEQ ID NO 1
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1
gaggtgcagc tgttggagtc tgggggaggc ttggtacagc ctgggggtc cctgagactc      60 tcctgtgcag cctctggatt caccttcaat aacgcctgga tgagctgggt ccgccaggct     120
ccagggaagg ggctggagtg ggtctcatcc attagtagta gtagtagtta catatactac     180
gcagactcag tgaagggccg attcaccatc tccagagaca attccaagaa cacgctgtat     240
ctgcaaatga acagcctgag agccgaggac actgccgtgt attactgtgc gagagtcagt     300
aggtactact acgaccatc tttctacttt gactcctggg gccagggtac actggtcacc     360
gtgagcagc                                                             369
```

<210> SEQ ID NO 2
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 2

```
cagtctgtgc tgactcagcc accctcagcg tctgggaccc ccgggcagag ggtcaccatc      60
tcctgctctg gaagcaggtc caacattggg aataattatg tatcctggta tcagcagctc     120
ccaggaacgg cccccaaact cctcatctat ggtaacaaca atcggccctc agggtccct      180 gaccgattct ctggctccaa gtctggcacc tcagcctccc tggccatcag tgggctccgg     240
tccgaggatg aggctgatta ttactgtgca gcatgggatg acagcctgaa tggtcattgg     300
gtgttcggcg gaggaaccaa gctgacggtc ctaggt                               336
```

<210> SEQ ID NO 3
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3

```
gaggtgcagc tgttggagtc tgggggaggc ttggtacagc ctgggggtc cctgagactc       60 tcctgtgcgg cctctggatt caccttcagt gactactaca tgagctgggt ccgccaggct     120
cccgggaagg ggctggagtg ggtatcgggt gttagttgga atggcagtag gacgcactat     180
gcagactctg tgaagggccg attcaccatc tccagagaca attccaagaa cacgctgtat     240
ctgcaaatga acagcctgag agccgaggac actgccgtgt attactgtgc gagagcggct     300
aggtactcct actactacta cggtatggac gtctggggcc aaggtacact ggtcaccgtg     360
agcagc                                                               366
```

<210> SEQ ID NO 4
<211> LENGTH: 327
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4

```
cagtctgtgc tgactcagcc accctcagcg tctgggaccc ccgggcagag ggtcaccatc      60
tcctgttctg gaagcagctc caacatcgga aataatgctg taaactggta tcagcagctc     120
ccaggaacgg cccccaaact cctcatctat gggaatgatc ggcggccctc agggtccct      180 gaccgattct ctggctccaa gtctggcacc tcagcctccc tggccatcag tgggctccgg     240
tccgaggatg aggctgatta ttactgtcag acctggggca ctggccgggg ggtattcggc     300
ggaggaacca agctgacggt cctaggt                                        327
```

<210> SEQ ID NO 5
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5

```
gaggtgcagc tgttggagtc tgggggaggc ttggtacagc ctggggggtc cctgagactc      60
tcctgtgcag cctctggatt cacctttagt agctattgga tgagctgggt ccgccaggct     120
ccagggaagg ggctggagtg gtctcaagt atcagtggta gtggtcgtag acatactac       180 gcagactccg tgcagggccg gttcaccatc tccagagaca attccaagaa cacgctgtat     240
ctgcaaatga acagcctgag agccgaggac actgccgtgt attactgtgc gagattggtc     300
tcctatggtt cggggagttt cggttttgac tactggggcc aaggtacact ggtcaccgtg     360
agcagc                                                                366
```

<210> SEQ ID NO 6
<211> LENGTH: 333
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 6

```
cagtctgtgc tgactcagcc accctcagcg tctgggaccc ccgggcagag ggtcaccatc      60
tcttgttctg gaagcagctc caatatcgga agtaattatg tatcctggta tcagcagctc     120
ccaggaacgg cccccaaact cctcatctat ggtaactaca tcggccctc aggggtccct     180 gaccgattct ctggctccaa gtctggcacc tcagcctccc tggccatcag tgggctccgg     240
tccgaggatg aggctgatta ttactgtgca gcatgggatg acagcctgag tggttgggtg     300
ttcggcggag gaaccaagct gacggtccta ggt                                   333
```

<210> SEQ ID NO 7
<211> LENGTH: 378
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 7

```
gaggtgcagc tgttggagtc tgggggaggc ttggtacagc ctggggggtc cctgagactc      60
tcctgtgcag cctctggatt caccttcagt aacgcctgga tgagctgggt ccgccaggtt     120
ccagggaagg ggctggagtg gtctcaact cttggtggta gtggtggtgg tagcacatac      180
tacgcagact ccgtgaaggg ccggttcacc atctccagag acaattccaa gaacacgctg     240
tatctgcaaa tgaacagcct gagagccgag gacactgccg tgtattactg tgcgaagtta     300 gggggcgat cccgatatgg gcggtggccc cgccaatttg actactgggg ccaaggtaca      360
ctggtcaccg tgagcagc                                                    378
```

<210> SEQ ID NO 8
<211> LENGTH: 333
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 8

```
cagtctgtgc tgactcagcc accctcagcg tctgggaccc ccgggcagag ggtcaccatc      60
tcctgctctg gaagcagctc caacattgga aataactatg tatcctggta tcagcagctc     120
```

```
ccaggaacgg cccccaaact cctcatctat agtaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgag tcattggctg    300
ttcggcggag gaaccaagct gacggtccta ggt                                 333

<210> SEQ ID NO 9
<211> LENGTH: 372
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 9
gaggtgcagc tgttggagtc tgggggaggc ttggtacagc ctggggggtc cctgagactc     60
tcctgtgcag cctctggatt caccttcagt gactactaca tgagctggat ccgccaggct    120
ccagggaagg ggctggagtg ggtctcaagt atcagtggcc gtgggggtag ttcctactac    180
gcagactccg tgaggggccg gttcaccatc tccagagaca attccaagaa cacgctgtat    240
ctgcaaatga acagcctgag agccgaggac actgccgtgt attactgtgc gagactttcc    300
tacagctatg gttacgaggg ggcctactac tttgactact ggggccaggg tacactggtc    360
accgtgagca gc                                                        372

<210> SEQ ID NO 10
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 10
cagtctgtgc tgactcagcc accctcagcg tctgggaccc ccgggcagag ggtcaccatc     60
tcctgctctg gaagcagctc caacattggg aataattatg tatcctggta tcagcagctc    120
ccaggaacgg cccccaaact cctcatctat aggaataatc agcggccctc aggggtccct    180
gaccgattct ctggctccaa gtctggcacc ttagcctccc tggccatcag tgggctccgg    240
tccgaggatg aggctgatta ttactgtgca acctgggatg acagcctgaa tggttgggtg    300
ttcggcggag gaaccaagct gacggtccta ggt                                 333

<210> SEQ ID NO 11
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 11
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcatcc attagtagta gtggtcgttt catttactac    180
gcagactcaa tgaagggccg cttcaccatc tccagagaca attccaagaa cacgctgtat    240
ctgcaaatga acagcctgag agccgaggac actgccgtgt attactgtac gaggctccgg    300
agagggagct acttctgggc ttttgatatc tggggccaag gtacactggt caccgtgagc    360
agc                                                                  363
```

<210> SEQ ID NO 12
<211> LENGTH: 333
<212> TYPE: DNA
<213> ORGANISM: Artificial Sequence
<220> FEATURE:
<223> OTHER INFORMATION: Description of Artificial Sequence: Synthetic
    nucleotide sequence

<400> SEQUENCE: 12
cagtctgtgc tgactcagcc accctcagcg tctgggaccc ccgggcagag ggtcaccatc     60
tcctgttctg gaagcagctc caacattggc ggtgagtctg tatcctggta tcagcagctc    120
ccaggaacgg cccccaaact cctcatctat agtaataatc agcggccctc agggtccct    180 gaccgattct ctggctccaa gtctggcacc tcagcctccc tggccatcag tgggctccgg    240
tccgaggatg aggctgatta ttactgtgca gcatgggatg acagcctgaa tggttgggtg    300
ttcggcggag gaaccaagct gacggtccta ggt                                 333

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 13
ggtgtgcatt ccgaggtgca gctgttggag                                      30

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 14
gacgtacgac tcacctgagc tcacggtgac cag                                  33

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 15
ggtgtgcatt cccagtctgt gctgactcag                                      30

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 16
gacgtacgtt ctactcacct aggaccgtca gctt                                 34

<210> SEQ ID NO 17
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 17
atgggtgaca atgacatc                                                   18

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aagcttgcta gcgtacg                                                    17

<210> SEQ ID NO 19
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 19
gaggtgcagc tgttggagtc tgggggaggc ttggtacagc ctgggggtc cctgagactc      60 tcctgtgcag cctctggatt cacctttaga acgtattgga tgacctgggt ccgccaggct    120
ccagggaagg ggctggagtg ggtctcatct attagcagta gcagtaatta catattctac    180
gcagactcag tgaagggccg attcaccatc tccagagaca attccaagaa cacgctgtat    240
ctgcaaatga acagcctgag agccgaggac actgccgtgt attactgtgc gagactcaga    300
cggagcagct ggtacggggg gtactggttc gaccccgg gccaaggtac actggtcacc    360
gtgagctca                                                           369

<210> SEQ ID NO 20
<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 20
cagtctgtgc tgactcagcc accctcagcg tctgggaccc ccgggcagag ggtcaccatc     60
tcctgctctg gaagcagctc aacattggg aataattatg tatcctggta tcagcagctc    120
ccaggaacgg cccccaaact cctcatctat aggaataatc agcggccctc aggggtccct    180
gaccgattct ctggctccaa gtctggcacc tcagcctccc tggccatcag tgggctccgg    240
tccgaggatg aggctgatta ttactgtgca gcatgggatg acagcctgaa tggtcattgg    300
gtgttcggcg gaggaaccaa gctgacggtc ctaggt                             336

<210> SEQ ID NO 21
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 21
```

```
gaggtgcagc tgttggagtc tggggggaggc ttggtacagc ctgggggttc cctgagactc        60
tcctgtgcag cctctggatt caccttcagt agcaactaca tgagctgggt ccgccaggct       120
ccagggaagg ggctggagtg ggtctcatcc attagtagta gtagtagtta catatactac       180
gcagactcag tgaagggccg attcaccatc tccagagaca attccaagaa cacgctgtat       240
ctgcaaatga acagcctgag agccgaggac actgccgtgt attactgtgc gagagtaggc       300
cggtataact ggaagacggg gcatgctttt gatatctggg gccagggtac actggtcacc       360
gtgagctca                                                                369
```

```
<210> SEQ ID NO 22
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 22
cagtctgtgc tgactcagcc accctcagcg tctgggaccc ccgggcagag ggtcaccatc        60
tcctgctctg gaaggaccta caacattgga aataattatg tatcgtggta tcagcagctc       120
ccaggaacgg cccccaaact cctcatctat ggtaacatca atcggcctc aggggtccct        180 gaccgattct ctggctccaa gtctggcacc tcagcctccc tggccatcag tgggctccgg       240
tccgaggatg aggctgatta ttactgtgca gcatgggatg tcaggctgaa tggttgggtg       300
ttcggcggag gaaccaagct gacggtccta ggt                                     333
```

```
<210> SEQ ID NO 23
<211> LENGTH: 381
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 23
gaggtgcagc tgttggagtc tggggggaggc ttggtacagc ctgggggggtc cctgagactc       60 tcctgtgcag cctctggatt caccttccgt gactactacg tgagctggat ccgccaggct       120
ccagggaagg ggctggagtg ggtctcaagt attagtggta gtgggggtag acatactac         180 gcagactccg tggagggccg gttcaccatc tccagagaca attccaagaa cacgctgtat       240
ctgcaaatga acagcctgag agccgaggac actgccatgt attactgtgc cagagtatcc       300
gcccttcgga gacccatgac tacagtaact acttactggt tcgaccctg gggccaaggt       360 acactggtca ccgtgagctc a                                                  381
```

```
<210> SEQ ID NO 24
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 24
cagtctgtgc tgactcagcc accctcagcg tctgggaccc ccgggcagag ggtcaccatc        60
tcctgctctg gaaggagctc caacattggg aatagttatg tctcctggta tcagcagctc       120
ccaggaacgg cccccaaact cctcatctat aggaataatc agcggccctc agggtccct        180
```

```
gaccgattct ctggctccaa gtctggcacc tcagcctccc tggccatcag tgggctccgg    240
tccgaggatg aggctgatta ttactgtgca ggatgggatg acaccctgcg tgcttgggtg    300
ttcggcggag gaaccaagct gacggtccta ggt                                 333
```

<210> SEQ ID NO 25
<211> LENGTH: 360
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 25

```
gaggtgcagc tgttggagtc tgggggaggc ttggtacagc ctgggggtc cctgagactc      60 tcctgtgcag cctctggatt caccttcagt aacgcctgga tgagctgggt ccgccaggct    120
ccagggaagg ggctgagtg gtctccgct attagtggta gtggtaacac atactatgca     180
gactccgtga agggccggtt caccatctcc agagacaatt ccaagaacac gctgtatctg    240
caaatgaaca gcctgagagc cgaggacact gccgtgtatt actgtgcgag agcctcccac    300
cgtatattag ttatgctttt tgatatctgg ggccagggta cactggtcac cgtgagctca    360
```

<210> SEQ ID NO 26
<211> LENGTH: 328
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 26

```
cagtctgtgc tgactcagcc accctcagcg tctgggaccc ccgggcagag ggtcaccatc     60
tcttgttctg gaagccgctc caacatcggg agaaatgctg ttagttggta tcagcagctc    120
ccaggaacgg cccccaaact cctcatctat gctaacagca tcggccctc aggggtccct     180 gaccgattct ctggctccaa gtctggcacc tcagcctccc tggccatcag tgggctccgg    240
tccgaggatg aggctgatta ttactgtgca gcatgggatg cagcctgaa tggttgggtg    300 ttcggcggag gaaccaagct gacggtcc                                       328
```

<210> SEQ ID NO 27
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 27

```
gaggtgcagc tgttggagtc tgggggaggc ttggtacagc ctgggggtc cctgagactc      60 tcctgtgcag cctctggatt caccttcagt aacgcctgga tgagctgggt ccgccaggct    120
ccagggaagg ggctggagtg gtctcaagt attagtgttg gtggacatag gacatattat     180
gcagattccg tgaagggccg gtccaccatc tccagagaca attccaagaa cacgctgtat    240
ctgcaaatga acagcctgag agccgaggac actgccgtgt attactgtgc acggatacgg    300
gtgggtccgt ccggcggggc ctttgactac tggggccagg gtacactggt caccgtgagc    360
tca                                                                  363
```

<210> SEQ ID NO 28
<211> LENGTH: 333

```
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 28
cagtctgtgc tgactcagcc accctcagcg tctgggaccc ccgggcagag ggtcaccatc    60
tcctgctctg gaagcaacac caacattggg aagaactatg tatcttggta tcagcagctc   120
ccaggaacgg cccccaaact cctcatctat gctaatagca atcggccctc aggggtccct   180
gaccgattct ctggctccaa gtctggcacc tcagcctccc tggccatcag tgggctccgg   240
tccgaggatg aggctgatta ttactgtgcg tcatgggatg ccagcctgaa tggtttgggta   300 ttcggcggag gaaccaagct gacggtccta ggt                                333

<210> SEQ ID NO 29
<211> LENGTH: 378
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 29
gaggtgcagc tgttggagtc tgggggaggc ttggtacagc ctggggggtc cctgagactc    60
tcctgtgcag cctctggatt caccttcagt aacgcctgga tgagctgggt ccgccaggct   120
ccagggaagg ggctggagtg gtctcatcc attagtagta gtagtagtta catatactac   180
gcagactcag tgaagggccg atccaccatc tccagagaca attccaagaa cacgctgtat   240
ctgcaaatga acagcctgag agccgaggac actgccgtgt attactgtgc gaggctcaca   300 aatatttga ctggttatta tacctcagga tatgcttttg atatctgggg ccaaggtaca   360
ctggtcaccg tgagctca                                                378

<210> SEQ ID NO 30
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 30
cagtctgtgc tgactcagcc accctcagcg tctgggaccc ccgggcagag ggtcaccatc    60
tcctgctctg gaagcacctc caacattggg aagaattatg tatcctggta tcagcagctc   120
ccaggaacgg cccccaaact cctcatctat ggtaacagca atcggccctc aggggtccct   180
gaccgattct ctggctccaa gtctggcacc tcagcctccc tggccatcag tgggctccgg   240
tccgaggatg aggctgatta ttactgtgca gcatggatg ccagcctcag tggttgggtg    300
ttcggcggag gaaccaagct gacggtccta ggt                                333

<210> SEQ ID NO 31
<211> LENGTH: 363
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 31
gaggtgcagc tgttggagtc tgggggaggc ttggtacagc ctggggggtc cctgagactc    60
```

```
tcctgtgcag cctctggatt caccttcagt agttcttgga tgagtttggt ccgccaggct      120
ccagggaagg ggctggagtg ggtctcatcc attagtagta gtagtagtta catatactac      180
gcagactcag tgaagggccg attcaccatc tccagagaca attccaagaa cacgctgtat      240
ctgcaaatga acagcctgag agccgaggac actgccgtgt attactgtgc gagagtaggg      300
aactacggtt ctaccacta catggacgtc tggggccaag gtacactggt caccgtgagc      360
tca                                                                   363

<210> SEQ ID NO 32
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 32
cagtctgtgc tgactcagcc accctcagcg tctgggaccc ccgggcagag ggtcaccatc      60
tcttgttctg gaggcagctc aaacatcgga aaaagaggtg taaattggta tcagcagctc      120
ccaggaacgg cccccaaact cctcatctat ggtaacagaa atcggccctc aggggtccct      180
gaccgattct ctggctccaa gtctggcacc tcagcctccc tggccatcag tgggctccgg      240
tccgaggatg aggctgatta ttactgtgct acatgggatt acagcctcaa tgcttgggtg      300
ttcggcggag gaaccaagct gacggtccta ggt                                  333

<210> SEQ ID NO 33
<211> LENGTH: 366
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 33
gaggtgcagc tgttggagtc tgggggaggc ttggtacagc ctgggggtc cctgagactc      60 tcctgtgcag cctctggatt caccttagt agctattgga tgagctgggt ccgccaggct      120
ccagggaagg ggctggagtg ggtctcatcc attagtagta gtagtagtta catatactac      180
gcagactcag tgaagggccg attcaccatc tccagagaca attccaagaa cacgctgtat      240
ctgcaaatga acagcctgag agccgaggac actgccgtgt attactgtgc gagaattaaa      300
cggttacgat tcggctggac cccttttgac tactggggcc agggtacact ggtcaccgtg      360
agctca                                                                366

<210> SEQ ID NO 34
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 34
cagtctgttc tgactcagcc accctcagcg tctgggaccc ccgggcagag ggtcaccatc      60
tcttgttctg gaagcagctc caacatcgga aataatggtg taaactggta tcagcagctc      120
ccaggaacgg cccccaaact cctcatctat ggtaacaaca atcggccctc aggggtccct      180
gaccgattct ctggctccaa gtctggcacc tcagcctccc tggccatcag tgggctccgg      240
```

```
<210> SEQ ID NO 35
<211> LENGTH: 369
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 35
gaggtgcagc tgttggagtc tgggggaggc ttggtacagc ctgggggtc cctgagactc        60 tcctgtgcag cctctggatt caccttcagt aacgcctgga tgagctgggt ccgccaggct      120
ccagggaagg ggctggagtg ggtctcatcc attagtagta gtagtagtta catatactac      180
gcagactcag tgaagggccg attcaccatc tccagagaca attccaagaa cacgctgtat      240
ctgcaaatga acagcctgag agccgaggac actgccgtgt attactgtgc gagagtcaat      300
agcaaaaagt ggtatgaggg ctacttcttt gactactggg gccagggtac actggtcacc      360
gtgagctca                                                              369

<210> SEQ ID NO 36
<211> LENGTH: 333
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 36
cagtctgtgc tgactcagcc accctcagcg tctgggaccc ccgggcagag ggtcaccatc       60
tcctgctctg gaagcagctc caacattggg aataattatg tatcctggta tcagcagctc      120
ccaggaacgg cccccaaact cctcatctat ggtaacagca tcggccctc aggggtccct       180 gaccgattct ctggctccaa gtctggcacc tcagcctccc tggccatcag tgggctccgg      240
tccgaggatg aggctgatta ttactgtgca gcatgggatg acagtctgag tggttgggtg      300
ttcggcggag gaaccaagct gacggtccta ggt                                   333

<210> SEQ ID NO 37
<211> LENGTH: 375
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 37
gaggtgcagc tgttggagtc tgggggaggc ttggtacagc ctgggggtc cctgagactc        60 tcctgtgcag cctctggatt caccttcagt aacgcctgga tgagctgggt ccgccaggct      120
ccagggaagg ggctggagtg ggtctcatcc attagtacta gtagtaatta catatactac      180
gcagactcag tgaagggccg gttcaccatc tccagagaca attccaagaa cacgctgtat      240
ctgcaaatga acagcctgag agccgaggac actgccgtgt attactgtgc gagagtcaag      300
aagtatagca gtggctggta ctcgaattat gcttttgata tctggggcca aggtacactg      360
gtcaccgtga gctca                                                       375

<210> SEQ ID NO 38
<211> LENGTH: 333
```

```
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 38
cagtctgtgc tgactcagcc accctcagcg tctgggaccc ccgggcagag ggtcaccatc    60
tcctgctctg gaagcagctc cagcattggg aataattttg tatcctggta tcagcagctc   120
ccaggaacgg cccccaaact cctcatctat gacaataata agcgaccctc agggttccct   180
gaccgattct ctggctccaa gtctggcacc tcagcctccc tggccatcag tgggctccgg   240
tccgaggatg aggctgatta ttactgtgca gcatgggatg acagcctgaa tggttgggtg   300
ttcggcggag gaaccaagct gacggtccta ggt                                333

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Phe Leu Asp Thr Val Tyr Gly Asn Cys Ser Thr His Phe Thr Val Lys
  1               5                  10                  15

Thr Arg Lys Gly
            20

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Gln Cys Ser Thr His Ile Leu Gln Trp Leu Lys Arg Val His Ala
  1               5                  10                  15

Asn Pro Leu Leu
            20

<210> SEQ ID NO 41
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Val Ile Ser Ile Pro Arg Leu Gln Ala Glu Ala Arg Ser Glu Ile Leu
  1               5                  10                  15

Ala His Trp Ser
            20

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 42

Lys Leu Val Lys Glu Ala Leu Lys Glu Ser Gln Leu Pro Thr Val Met
 1               5                  10                  15

Asp Phe Arg Lys
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Lys Phe Val Thr Gln Ala Glu Gly Ala Lys Gln Thr Glu Ala Thr
 1               5                  10                  15

Met Thr Phe Lys
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Gly Ser Leu Arg His Lys Phe Leu Asp Ser Asn Ile Lys Phe Ser
 1               5                  10                  15

His Val Glu Lys
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Gly Thr Tyr Gly Leu Ser Cys Gln Arg Asp Pro Asn Thr Gly Arg
 1               5                  10                  15

Leu Asn Gly Glu
            20

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Leu Asn Gly Glu Ser Asn Leu Arg Phe Asn Ser Ser Tyr Leu Gln
 1               5                  10                  15

Gly Thr Asn Gln
            20

<210> SEQ ID NO 47
<211> LENGTH: 20
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 47

Ser Leu Thr Ser Thr Ser Asp Leu Gln Ser Gly Ile Ile Lys Asn Thr
 1               5                  10                  15

Ala Ser Leu Lys
            20

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Ala Ser Leu Lys Tyr Glu Asn Tyr Glu Leu Thr Leu Lys Ser Asp
 1               5                  10                  15

Thr Asn Gly Lys
            20

<210> SEQ ID NO 49
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Met Thr Phe Ser Lys Gln Asn Ala Leu Leu Arg Ser Glu Tyr Gln
 1               5                  10                  15

Ala Asp Tyr Glu
            20

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Met Lys Val Lys Ile Ile Arg Thr Ile Asp Gln Met Gln Asn Ser Glu
 1               5                  10                  15

Leu Gln Trp Pro
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Ala Leu Asp Asp Ala Lys Ile Asn Phe Asn Glu Lys Leu Ser Gln
 1               5                  10                  15

Leu Gln Thr Tyr
            20

<210> SEQ ID NO 52
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Thr Thr Lys Gln Ser Phe Asp Leu Ser Val Lys Ala Gln Tyr Lys
 1               5                  10                  15

Lys Asn Lys His
            20

<210> SEQ ID NO 53
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Glu Glu Glu Met Leu Glu Asn Val Ser Leu Val Cys Pro Lys Asp Ala
 1               5                  10                  15

Thr Arg Phe Lys
            20

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Thr Ser His His Leu Val Ser Arg Lys Ser Ile Ser Ala Ala
 1               5                  10                  15

Leu Glu His Lys
            20

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Glu Asn Ile Asp Phe Asn Lys Ser Gly Ser Ser Thr Ala Ser Trp
 1               5                  10                  15

Ile Gln Asn Val
            20

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ile Arg Glu Val Thr Gln Arg Leu Asn Gly Glu Ile Gln Ala Leu Glu
1               5                   10                  15

Leu Pro Gln Lys
            20
```

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Glu Val Asp Val Leu Thr Lys Tyr Ser Gln Pro Glu Asp Ser Leu Ile
1               5                   10                  15

Pro Phe Phe Glu
            20
```

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
His Thr Phe Leu Ile Tyr Ile Thr Glu Leu Leu Lys Lys Leu Gln Ser
1               5                   10                  15

Thr Thr Val Met
            20
```

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Leu Leu Asp Ile Ala Asn Tyr Leu Met Glu Gln Ile Gln Asp Asp Cys
1               5                   10                  15

Thr Gly Asp Glu
            20
```

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Cys Thr Gly Asp Glu Asp Tyr Thr Tyr Lys Ile Lys Arg Val Ile Gly
1               5                   10                  15

Asn Met Gly Gln
            20
```

<210> SEQ ID NO 61
<211> LENGTH: 20
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 61

Gly Asn Met Gly Gln Thr Met Glu Gln Leu Thr Pro Glu Leu Lys Ser
1               5                   10                  15

Ser Ile Leu Lys
            20

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ser Ile Leu Lys Cys Val Gln Ser Thr Lys Pro Ser Leu Met Ile
1               5                   10                  15

Gln Lys Ala Ala
            20

<210> SEQ ID NO 63
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Gln Lys Ala Ala Ile Gln Ala Leu Arg Lys Met Glu Pro Lys Asp
1               5                   10                  15

Lys Asp Gln Glu
            20

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Leu Asn Gly Glu Ser Asn Leu Arg Phe Asn Ser Ser Tyr Leu Gln
1               5                   10                  15

Gly Thr Asn Gln
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Leu Asn Ser His Gly Leu Glu Leu Asn Ala Asp Ile Leu Gly Thr
1               5                   10                  15

Asp Lys Ile Asn
            20

```
<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Ile Gln Asn Val Asp Thr Lys Tyr Gln Ile Arg Ile Gln Ile Gln
1               5                   10                  15

Glu Lys Leu Gln
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Tyr Ile Ser Asp Trp Trp Thr Leu Ala Ala Lys Asn Leu Thr Asp
1               5                   10                  15

Phe Ala Glu Gln
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Ala Thr Leu Gln Arg Ile Tyr Ser Leu Trp Glu His Ser Thr Lys
1               5                   10                  15

Asn His Leu Gln
            20

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Leu Leu Val Pro Pro Glu Thr Glu Glu Ala Lys Gln Val Leu Phe
1               5                   10                  15

Leu Asp Thr Val
            20

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Glu Ile Gly Leu Glu Gly Lys Gly Phe Glu Pro Thr Leu Glu Ala
1               5                   10                  15
```

```
Leu Phe Gly Lys
            20

<210> SEQ ID NO 71
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Gly Ala Ser Met Lys Leu Thr Thr Asn Gly Arg Phe Arg Glu His
1               5                   10                  15

Asn Ala Lys Phe
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asn Leu Ile Gly Asp Phe Glu Val Ala Glu Lys Ile Asn Ala Phe Arg
1               5                   10                  15

Ala Lys Val His
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly His Ser Val Leu Thr Ala Lys Gly Met Ala Leu Phe Gly Glu Gly
1               5                   10                  15

Lys Ala Glu Phe
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Phe Lys Ser Ser Val Ile Thr Leu Asn Thr Asn Ala Glu Leu Phe Asn
1               5                   10                  15

Gln Ser Asp Ile
            20

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 75

Phe Pro Asp Leu Gly Gln Glu Val Ala Leu Asn Ala Asn Thr Lys Asn
 1               5                  10                  15

Gln Lys Ile Arg
            20

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cccagtcacg acgttgtaaa acg                                            23

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gaaacagcta tgaaatacct attgc                                          25

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
caggaaacag ctatgac                                                   17

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
agacccaagc tagcttggta c                                              21
```